United States Patent
Chen et al.

(10) Patent No.: US 12,377,155 B2
(45) Date of Patent: Aug. 5, 2025

(54) BICYCLIC PEPTIDE LIGANDS SPECIFIC FOR PSMA

(71) Applicant: BicycleRD Limited, Cambridge (GB)

(72) Inventors: Liuhong Chen, Cambridge (GB); Catherine Stace, Cambridge (GB); Daniel Teufel, Cambridge (GB); Punit Upadhyaya, Lexington, MA (US); Edward Walker, Cambridge (GB)

(73) Assignee: BicycleRD Limited, Cambridge (GB)

( * ) Notice: Subject to any disclaimer, the term of this patent is extended or adjusted under 35 U.S.C. 154(b) by 790 days.

(21) Appl. No.: 17/309,630

(22) PCT Filed: Dec. 13, 2019

(86) PCT No.: PCT/GB2019/053536
§ 371 (c)(1),
(2) Date: Jun. 11, 2021

(87) PCT Pub. No.: WO2020/120980
PCT Pub. Date: Jun. 18, 2020

(65) Prior Publication Data
US 2022/0054646 A1    Feb. 24, 2022

(30) Foreign Application Priority Data
Dec. 13, 2018   (GB) ..................... 1820325

(51) Int. Cl.
A61K 47/64   (2017.01)
C07K 7/64    (2006.01)

(52) U.S. Cl.
CPC ............... *A61K 47/64* (2017.08); *C07K 7/64* (2013.01)

(58) Field of Classification Search
CPC .................................. A61K 47/64; C07K 7/64
See application file for complete search history.

(56) References Cited

U.S. PATENT DOCUMENTS

| | | |
|---|---|---|
| 2,642,514 A | 6/1953 | Herkenhoff |
| 4,650,750 A | 3/1987 | Giese |
| 4,709,016 A | 11/1987 | Giese |
| 5,360,819 A | 11/1994 | Giese |
| 5,516,931 A | 5/1996 | Giese et al. |
| 5,595,756 A | 1/1997 | Bally et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 6,326,144 B1 | 12/2001 | Bawendi et al. |
| 6,468,808 B1 | 10/2002 | Nie et al. |
| 6,552,065 B2 | 4/2003 | Remiszewski et al. |
| 7,151,047 B2 | 12/2006 | Chan et al. |
| 7,192,785 B2 | 3/2007 | Nie et al. |
| 7,390,799 B2 | 6/2008 | Bruncko et al. |
| 8,138,347 B2 | 3/2012 | Adams et al. |
| 8,680,022 B2 | 3/2014 | Gregory et al. |
| 8,685,890 B2 | 4/2014 | Winter et al. |
| 8,778,844 B2 | 7/2014 | Winter et al. |
| 8,906,682 B2 | 12/2014 | June et al. |
| 8,986,655 B2 | 3/2015 | Weiss et al. |
| 9,518,081 B2 | 12/2016 | Winter et al. |
| 9,644,201 B2 | 5/2017 | Winter et al. |
| 9,657,288 B2 | 5/2017 | Winter et al. |
| 9,670,482 B2 | 6/2017 | Winter et al. |
| 9,670,484 B2 | 6/2017 | Winter et al. |
| 9,670,521 B2 | 6/2017 | Grabstein et al. |
| 9,868,767 B2 | 1/2018 | Pei et al. |
| 9,932,367 B2 | 4/2018 | Stace et al. |
| 9,994,617 B2 | 6/2018 | Tite et al. |
| 10,118,947 B2 | 11/2018 | Teufel et al. |
| 10,294,274 B2 | 5/2019 | Teufel et al. |
| 10,441,663 B2 | 10/2019 | Bennett et al. |
| 10,532,106 B2 | 1/2020 | Teufel et al. |
| 10,624,968 B2 | 4/2020 | Bennett et al. |
| 10,626,147 B2 | 4/2020 | Pei et al. |
| 10,792,368 B1 | 10/2020 | Teufel et al. |
| 10,800,813 B2 | 10/2020 | Tite et al. |
| 10,857,196 B2 | 12/2020 | Beswick et al. |
| 10,870,679 B2 | 12/2020 | Teufel et al. |
| 10,875,894 B2 | 12/2020 | Chen et al. |
| 10,894,808 B2 | 1/2021 | Teufel et al. |
| 10,899,798 B2 | 1/2021 | Bennett et al. |
| 10,919,937 B2 | 2/2021 | Beswick et al. |
| 10,994,019 B2 | 5/2021 | Teufel et al. |
| 11,103,591 B2 | 8/2021 | Teufel et al. |
| 11,180,531 B2 | 11/2021 | Beswick et al. |
| 11,261,214 B2 | 1/2022 | Chen et al. |
| 11,484,602 B2 | 1/2022 | Chen et al. |
| 11,306,123 B2 | 4/2022 | Mudd et al. |
| 11,312,749 B2 | 4/2022 | Mudd et al. |

(Continued)

FOREIGN PATENT DOCUMENTS

| | | |
|---|---|---|
| CN | 101497878 A | 5/2009 |
| CN | 105307686 A | 2/2016 |

(Continued)

OTHER PUBLICATIONS

Adams et al., "Big Opportunities for Small Molecules in Immuno-oncology," Nature Reviews, 2015, 14:603-622.

(Continued)

*Primary Examiner* — Amber D Steele
(74) *Attorney, Agent, or Firm* — Wolf, Greenfield & Sacks, P.C.

(57) ABSTRACT

The present invention relates to polypeptides which are covalently bound to molecular scaffolds such that two or more peptide loops are subtended between attachment points to the scaffold. In particular, the invention describes peptides which are high affinity binders of prostrate-specific membrane antigen (PSMA). The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by PSMA.

14 Claims, No Drawings
Specification includes a Sequence Listing.

(56) References Cited

U.S. PATENT DOCUMENTS

| | | |
|---|---|---|
| 11,332,500 B2 | 5/2022 | Mudd et al. |
| 11,396,530 B2 | 7/2022 | Beswick et al. |
| 11,241,473 B2 | 8/2022 | Beswick et al. |
| 11,414,488 B2 | 8/2022 | Bennett et al. |
| 11,433,137 B2 | 9/2022 | Bennett et al. |
| 11,453,702 B2 | 9/2022 | Beswick et al. |
| 11,453,703 B2 | 9/2022 | Keen et al. |
| 11,542,304 B2 | 3/2023 | Chen et al. |
| 11,613,560 B2 | 3/2023 | Stephen et al. |
| 11,746,126 B2 | 5/2023 | Bennett et al. |
| 11,672,868 B2 | 6/2023 | Teufel et al. |
| 11,730,819 B2 | 8/2023 | Teufel et al. |
| 11,623,012 B2 | 11/2023 | Chen et al. |
| 11,696,956 B2 | 11/2023 | Chen et al. |
| 11,814,447 B2 | 11/2023 | Teufel et al. |
| 11,833,211 B2 | 12/2023 | Chen et al. |
| 11,912,792 B2 | 2/2024 | Beswick et al. |
| 11,946,041 B2 | 4/2024 | Chen et al. |
| 11,970,553 B2 | 4/2024 | Mudd et al. |
| 12,049,520 B2 | 7/2024 | Chen et al. |
| 2002/0164788 A1 | 11/2002 | Ellis et al. |
| 2005/0169931 A1 | 8/2005 | Kinch et al. |
| 2009/0222937 A1 | 3/2009 | Arnould et al. |
| 2009/0304721 A1 | 10/2009 | Kinch et al. |
| 2012/0101253 A1* | 4/2012 | Heinis .................... A61K 47/64 530/317 |
| 2012/0172235 A1 | 5/2012 | Winter et al. |
| 2013/0064791 A1 | 3/2013 | Poelstra et al. |
| 2013/0072598 A1 | 3/2013 | Yang et al. |
| 2014/0249292 A1 | 9/2014 | Tite et al. |
| 2014/0274759 A1 | 9/2014 | Walker et al. |
| 2014/0256596 A1 | 11/2014 | Tite et al. |
| 2014/0163201 A1 | 12/2014 | Winter et al. |
| 2015/0087810 A1 | 3/2015 | Moore et al. |
| 2015/0038434 A1 | 5/2015 | Yang et al. |
| 2016/0046721 A1 | 2/2016 | Qian et al. |
| 2016/0031939 A1 | 4/2016 | Stace et al. |
| 2016/0122430 A1 | 5/2016 | Gish et al. |
| 2016/0256579 A1 | 8/2016 | Shalom |
| 2016/0326232 A1* | 11/2016 | Rosa ....................... A61K 51/08 |
| 2017/0067045 A1 | 3/2017 | Winter et al. |
| 2017/0190743 A1 | 7/2017 | Pei et al. |
| 2017/0204150 A1* | 7/2017 | Liu ........................ C07K 14/71 |
| 2017/0304342 A1* | 10/2017 | Cox ...................... A61K 9/0053 |
| 2017/0306032 A1 | 10/2017 | Gehlsen |
| 2017/0360952 A1 | 12/2017 | Schwartz et al. |
| 2018/0280525 A1 | 4/2018 | Teufel et al. |
| 2018/0169254 A1 | 6/2018 | Bennett et al. |
| 2018/0200378 A1 | 7/2018 | Bennett et al. |
| 2018/0318451 A1 | 8/2018 | Skerra et al. |
| 2018/0311300 A1 | 11/2018 | Beswick et al. |
| 2018/0362585 A1 | 12/2018 | Teufel et al. |
| 2018/0371020 A1 | 12/2018 | Bennett et al. |
| 2019/0134213 A1 | 5/2019 | Teufel et al. |
| 2019/0184025 A1 | 6/2019 | Chen et al. |
| 2019/0263866 A1 | 8/2019 | Chen et al. |
| 2019/0307836 A1 | 10/2019 | Keen et al. |
| 2019/0389906 A1 | 12/2019 | Beswick et al. |
| 2019/0389907 A1 | 12/2019 | Teufel et al. |
| 2020/0129630 A1 | 4/2020 | Koehler et al. |
| 2020/0131228 A1 | 4/2020 | Beswick et al. |
| 2020/0171161 A1 | 6/2020 | Teufel et al. |
| 2020/0190213 A1 | 6/2020 | Preyer et al. |
| 2020/0215199 A1 | 7/2020 | Bennett et al. |
| 2020/0255477 A1 | 8/2020 | Chen et al. |
| 2020/0289657 A1 | 9/2020 | Teufel et al. |
| 2020/0291096 A1 | 9/2020 | Keen et al. |
| 2020/0283482 A1 | 10/2020 | Keen et al. |
| 2020/0316209 A1 | 10/2020 | Teufel et al. |
| 2020/0338203 A1 | 10/2020 | Chen et al. |
| 2020/0354406 A1 | 11/2020 | Stephen et al. |
| 2020/0354456 A1 | 11/2020 | Bennett et al. |
| 2020/0407709 A1 | 12/2020 | Chen et al. |
| 2021/0040154 A1 | 2/2021 | Mudd et al. |
| 2021/0046145 A1 | 2/2021 | Beswick et al. |
| 2021/0069287 A1 | 3/2021 | Mudd et al. |
| 2021/0079045 A1 | 3/2021 | Bennett et al. |
| 2021/0101932 A1 | 4/2021 | Chen et al. |
| 2021/0101933 A1 | 4/2021 | Chen et al. |
| 2021/0101937 A1 | 4/2021 | Mudd et al. |
| 2021/0122785 A1 | 4/2021 | Teufel et al. |
| 2021/0122804 A1 | 4/2021 | Teufel et al. |
| 2021/0147484 A1 | 5/2021 | Beswick et al. |
| 2021/0147485 A1 | 5/2021 | Teufel et al. |
| 2021/0261620 A1 | 8/2021 | Teufel et al. |
| 2021/0269480 A1 | 9/2021 | Beswick et al. |
| 2021/0299210 A2 | 9/2021 | Keen et al. |
| 2022/0023432 A1 | 1/2022 | Teufel et al. |
| 2022/0024982 A1 | 1/2022 | Chen et al. |
| 2022/0054646 A1 | 2/2022 | Chen et al. |
| 2022/0031858 A1 | 3/2022 | Mcdonnell et al. |
| 2022/0064218 A1 | 3/2022 | Baldassarre et al. |
| 2022/0064221 A1 | 3/2022 | Lani et al. |
| 2022/0088118 A1 | 3/2022 | Baldassarre et al. |
| 2022/0088207 A1 | 3/2022 | Chen et al. |
| 2022/0089643 A1 | 3/2022 | Beswick et al. |
| 2022/0119488 A1 | 4/2022 | Lani et al. |
| 2022/0133732 A1 | 5/2022 | Baldassarre et al. |
| 2022/0133733 A1 | 5/2022 | Baldassarre et al. |
| 2022/0135614 A1 | 5/2022 | Teufel et al. |
| 2022/0184222 A1 | 6/2022 | Bennett et al. |
| 2022/0194983 A1 | 6/2022 | Teufel et al. |
| 2022/0213145 A1 | 7/2022 | Chen et al. |
| 2022/0227811 A1 | 7/2022 | Mudd et al. |
| 2022/0242911 A1 | 8/2022 | Mudd et al. |
| 2022/0257784 A1 | 8/2022 | Upadhyaya et al. |
| 2022/0281918 A1 | 8/2022 | Van Rietschoten et al. |
| 2022/0387611 A1 | 8/2022 | Bennett et al. |
| 2022/0275053 A1 | 9/2022 | Upadhyaya et al. |
| 2022/0289792 A1 | 9/2022 | Chen et al. |
| 2022/0306689 A9 | 9/2022 | Chen et al. |
| 2022/0306694 A1 | 9/2022 | Mudd et al. |
| 2022/0072140 A1 | 10/2022 | Stace et al. |
| 2022/0362390 A1 | 11/2022 | Stace et al. |
| 2023/0002596 A1 | 1/2023 | Zhang et al. |
| 2023/0008076 A1 | 1/2023 | Keen et al. |
| 2023/0025916 A1 | 1/2023 | Bennett et al. |
| 2023/0025971 A1 | 1/2023 | Bennett et al. |
| 2023/0165966 A1 | 1/2023 | Koehler et al. |
| 2023/0086865 A1 | 3/2023 | Balmford et al. |
| 2023/0129258 A1 | 4/2023 | Upadhyaya et al. |
| 2023/0106511 A1 | 6/2023 | Balmford et al. |
| 2023/0181749 A1 | 6/2023 | Dickson et al. |
| 2023/0220008 A1 | 7/2023 | Chen et al. |
| 2023/0233698 A1 | 7/2023 | Bennett et al. |
| 2023/0287047 A1 | 9/2023 | Beswick et al. |
| 2023/0340020 A1 | 10/2023 | Teufel et al. |
| 2023/0144799 A1 | 11/2023 | Chen et al. |
| 2024/0082410 A1 | 3/2024 | Teufel et al. |
| 2024/0000957 A1 | 4/2024 | Chen et al. |
| 2024/0108738 A1 | 4/2024 | Keen et al. |
| 2024/0158444 A1 | 5/2024 | Bennett et al. |
| 2024/0173422 A1 | 5/2024 | Beswick et al. |
| 2024/0189436 A1 | 6/2024 | Chen et al. |
| 2024/0197897 A1 | 6/2024 | Keen et al. |
| 2024/0240255 A1 | 7/2024 | Blakemore et al. |
| 2024/0325554 A1 | 10/2024 | Keen et al. |
| 2024/0336656 A1 | 10/2024 | Mudd et al. |
| 2024/0400616 A1 | 12/2024 | Beswick et al. |

FOREIGN PATENT DOCUMENTS

| | | |
|---|---|---|
| EP | 2393520 A1 | 12/2011 |
| EP | 2970954 A1 | 1/2016 |
| EP | 3192802 A1 | 7/2017 |
| FR | 2932189 A1 | 11/2009 |
| GB | 1239978 A | 7/1971 |
| JP | 2006514104 A | 4/2006 |
| JP | 2011513298 A | 4/2011 |
| JP | 2011522794 A | 4/2011 |
| WO | WO9708320 A1 | 6/1997 |
| WO | WO9819705 A1 | 5/1998 |
| WO | WO0128683 A1 | 4/2001 |
| WO | WO0142246 A2 | 6/2001 |

(56) References Cited

FOREIGN PATENT DOCUMENTS

| | | | | |
|---|---|---|---|---|
| WO | WO0363794 | A2 | 8/2003 | |
| WO | WO2004005348 | A1 | 1/2004 | |
| WO | WO2004019973 | A1 | 3/2004 | |
| WO | WO0288112 | A1 | 8/2004 | |
| WO | WO-2004077062 | A2 * | 9/2004 | ............. C07K 17/02 |
| WO | WO2004089925 | A1 | 10/2004 | |
| WO | WO2004106328 | A1 | 12/2004 | |
| WO | WO2005007623 | A2 | 1/2005 | |
| WO | WO2005103083 | A2 | 11/2005 | |
| WO | WO2005113554 | A2 | 12/2005 | |
| WO | WO2006029879 | A2 | 3/2006 | |
| WO | WO-2006078161 | A1 * | 7/2006 | ............. A61P 15/16 |
| WO | WO2006078846 | A1 | 7/2006 | |
| WO | WO2006101187 | A1 | 9/2006 | |
| WO | WO2006105021 | A2 | 10/2006 | |
| WO | WO2006122806 | A2 | 11/2006 | |
| WO | WO2007016176 | A2 | 2/2007 | |
| WO | WO2007044729 | A2 | 4/2007 | |
| WO | WO2007053452 | A1 | 5/2007 | |
| WO | WO2007070514 | A1 | 6/2007 | |
| WO | WO2007005874 | A2 | 7/2007 | |
| WO | WO2007084786 | A1 | 7/2007 | |
| WO | WO2007129161 | A2 | 11/2007 | |
| WO | WO2008033561 | A2 | 3/2008 | |
| WO | WO2008039218 | A2 | 4/2008 | |
| WO | WO2008089627 | A1 | 7/2008 | |
| WO | WO2008109943 | A1 | 9/2008 | |
| WO | WO2008118802 | A1 | 10/2008 | |
| WO | 2008134761 | A2 | 11/2008 | |
| WO | WO2008132601 | A1 | 11/2008 | |
| WO | WO2008157490 | A1 | 12/2008 | |
| WO | WO2009009116 | A2 | 1/2009 | |
| WO | WO2009044273 | A2 | 4/2009 | |
| WO | WO2009073620 | A2 | 6/2009 | |
| WO | 2009098450 | A2 | 8/2009 | |
| WO | WO2009097397 | A2 | 8/2009 | |
| WO | WO2009114512 | A1 | 9/2009 | |
| WO | WO2010019570 | A2 | 2/2010 | |
| WO | WO2010077634 | A1 | 7/2010 | |
| WO | WO2010089115 | A1 | 8/2010 | |
| WO | WO2010089117 | A1 | 12/2010 | |
| WO | WO2011018227 | A2 | 2/2011 | |
| WO | WO2011028683 | A1 | 3/2011 | |
| WO | WO2011056652 | A1 | 5/2011 | |
| WO | WO2011070024 | A1 | 6/2011 | |
| WO | WO2011079015 | A1 | 6/2011 | |
| WO | WO2011090760 | A1 | 7/2011 | |
| WO | WO2011107553 | A1 | 9/2011 | |
| WO | WO2011109400 | A2 | 9/2011 | |
| WO | WO2011131407 | A1 | 10/2011 | |
| WO | WO2011140249 | A2 | 11/2011 | |
| WO | WO2012032433 | A1 | 3/2012 | |
| WO | WO2012057624 | A1 | 5/2012 | |
| WO | WO2012142237 | A1 | 10/2012 | |
| WO | WO2012145493 | A1 | 10/2012 | |
| WO | WO2013050615 | A1 | 4/2013 | |
| WO | WO2013050617 | A1 | 4/2013 | |
| WO | WO2013079174 | A1 | 6/2013 | |
| WO | WO2013087699 | A1 | 6/2013 | |
| WO | WO2013119716 | A1 | 8/2013 | |
| WO | WO2013132044 | A1 | 9/2013 | |
| WO | WO2013050616 | A1 | 11/2013 | |
| WO | WO2013169264 | A1 | 11/2013 | |
| WO | WO2014008218 | A1 | 1/2014 | |
| WO | WO2014036357 | A1 | 3/2014 | |
| WO | WO2014044872 | A1 | 3/2014 | |
| WO | WO2014063012 | A1 | 4/2014 | |
| WO | WO2014142237 | A1 | 9/2014 | |
| WO | WO2014164693 | A2 | 10/2014 | |
| WO | WO2014167122 | A1 | 10/2014 | |
| WO | WO2014190257 | A2 | 11/2014 | |
| WO | WO2015116904 | A1 | 6/2015 | |
| WO | WO2015171938 | A1 | 11/2015 | |
| WO | WO2015179691 | A2 | 11/2015 | |
| WO | WO2016046574 | A1 | 3/2016 | |
| WO | 2016067035 | A1 | 5/2016 | |
| WO | WO2016050361 | A1 | 7/2016 | |
| WO | WO2016171242 | A1 | 10/2016 | |
| WO | WO2016171272 | A1 | 10/2016 | |
| WO | WO2016174103 | A1 | 11/2016 | |
| WO | WO2017046658 | A1 | 3/2017 | |
| WO | WO2017102906 | A1 | 6/2017 | |
| WO | WO2017161069 | A1 | 9/2017 | |
| WO | WO2017173408 | A1 | 10/2017 | |
| WO | WO2017182672 | A1 | 10/2017 | |
| WO | WO2017191460 | A1 | 11/2017 | |
| WO | WO2017205738 | A1 | 11/2017 | |
| WO | WO2018096365 | A1 | 5/2018 | |
| WO | 2018115203 | A1 | 6/2018 | |
| WO | WO2018115204 | A1 | 6/2018 | |
| WO | WO2018222987 | A1 | 6/2018 | |
| WO | WO2018127699 | A1 | 7/2018 | |
| WO | WO2018156740 | A1 | 8/2018 | |
| WO | WO2018197509 | A1 | 11/2018 | |
| WO | WO2018197893 | A1 | 11/2018 | |
| WO | 2019002842 | A1 | 1/2019 | |
| WO | WO2019025811 | A1 | 2/2019 | |
| WO | WO2019034866 | A1 | 2/2019 | |
| WO | WO2019034868 | A1 | 2/2019 | |
| WO | WO2019084060 | A1 | 2/2019 | |
| WO | WO2019094395 | A2 | 5/2019 | |
| WO | WO2019122860 | A1 | 6/2019 | |
| WO | WO2019122861 | A1 | 6/2019 | |
| WO | WO2019122863 | A1 | 6/2019 | |
| WO | WO2019162682 | A1 | 8/2019 | |
| WO | WO2019193328 | A1 | 10/2019 | |
| WO | WO2019136442 | A1 | 11/2019 | |
| WO | WO2019226617 | A1 | 11/2019 | |
| WO | 2019243455 | A1 | 12/2019 | |
| WO | WO2019243313 | A1 | 12/2019 | |
| WO | WO2019243329 | A1 | 12/2019 | |
| WO | WO2019243353 | A1 | 12/2019 | |
| WO | WO2019243832 | A1 | 12/2019 | |
| WO | WO2019243833 | A1 | 12/2019 | |
| WO | WO2020084305 | A1 | 4/2020 | |
| WO | WO2020089627 | A1 | 5/2020 | |
| WO | 2020120980 | A1 | 6/2020 | |
| WO | WO2020120981 | A1 | 6/2020 | |
| WO | WO2020120983 | A1 | 6/2020 | |
| WO | WO2020120984 | A1 | 6/2020 | |
| WO | WO2020128526 | A1 | 6/2020 | |
| WO | WO2020128527 | A1 | 6/2020 | |
| WO | WO2020148525 | A1 | 7/2020 | |
| WO | WO2020148526 | A1 | 7/2020 | |
| WO | WO2020148527 | A1 | 7/2020 | |
| WO | WO2020148528 | A1 | 7/2020 | |
| WO | WO2020148529 | A1 | 7/2020 | |
| WO | WO2020148530 | A1 | 7/2020 | |
| WO | WO2020165600 | A1 | 8/2020 | |
| WO | WO2020178574 | A1 | 9/2020 | |
| WO | WO2020201753 | A1 | 10/2020 | |
| WO | WO2020225577 | A1 | 11/2020 | |
| WO | WO2020229803 | A1 | 11/2020 | |
| WO | WO2021019243 | A1 | 2/2021 | |
| WO | WO2021019244 | A1 | 2/2021 | |
| WO | WO2021019245 | A1 | 2/2021 | |
| WO | WO2021019246 | A1 | 2/2021 | |
| WO | WO2021028686 | A1 | 2/2021 | |
| WO | WO2021171028 | A1 | 2/2021 | |
| WO | WO2021171029 | A1 | 2/2021 | |
| WO | WO2021038232 | A1 | 4/2021 | |
| WO | WO2021064428 | A1 | 4/2021 | |
| WO | WO2021074622 | A1 | 4/2021 | |
| WO | WO2021074647 | A1 | 4/2021 | |
| WO | WO2021105694 | A1 | 6/2021 | |
| WO | WO2021148974 | A1 | 7/2021 | |
| WO | WO2021234391 | A1 | 11/2021 | |
| WO | WO2021250418 | A1 | 12/2021 | |
| WO | WO2022038158 | A1 | 2/2022 | |
| WO | WO2022148969 | A1 | 7/2022 | |
| WO | WO2022148974 | A2 | 7/2022 | |
| WO | WO2022148975 | A1 | 7/2022 | |
| WO | WO2022148979 | A1 | 7/2022 | |

(56) References Cited

FOREIGN PATENT DOCUMENTS

| WO | WO2022029420 A1 | 10/2022 |
| WO | WO2023089308 A1 | 5/2023 |
| WO | WO2023031623 A2 | 9/2023 |

OTHER PUBLICATIONS

Adams, "Molecular control of arterial-venous blood vessel identity," Journal of Anatomy, 2003, 202(1):105-112.
Akanuma et al., "MicroRNA-133a regulates the mRNAs of two invadopodia-related proteins, FSCN1 and MMP14, in esophageal cancer," Br J Cancer. Jan. 7, 2014;110(1 ), 189-98.
Angelini et al., "Bicyclic peptide inhibitor reveals large contact interface with a protease target." ACS chemical biology 7, No. 5 (2012): 817-821.
Annunziata et al., "Phase 1, open-label study of MEDI-547 in patients with relapsed or refractorysolid tumors," Invest New Druas, Feb. 2013, 31(1):77-84.
Anonymous, "Bicycle Conjugates", URL:https://web.archive.org/web/20210104063050/https://www.bicycletherapeutics.co m/programs , 2021, 4 pages.
Anonymous, "Bicycle Therapeutics to Present New Translational Research for BT5528 and Preclinical Data for Tumor-targeted Immune Cell Agonists at the AACR Virtual Annual Meeting II," May 15, 2020; 2 pages. URL:https://www.businesswire.com/news/home/20200515005111/en/Bicycle-Therapeutics- to-Present-New-Translational-Research-for-BT5528-and-Preelinical-Data-for-Tumor-targeted-Immune-Cell-Aaon ists-at-the-AACR-Virtual-Ann ual-Meetina-II.
Anonymous, "Constrained Peptides Unconstrained Thinking Forward-Looking Statements", URL: https://investors.bicycletherapeutics.com/static-files/5f7f462f-2417-439d-b829-d723b3fd65f7, Aug. 2019, 26 pages.
Anthony et al., "Recapitulation of IVIG anti-inflammatory activity with a recombinant IgG Fc", Science Apr. 18, 2008;320(5874):373-376.
Arkadash et al., "Development of High Affinity and High Specificity Inhibitors of |Matrix Metalloproteinase 14 through Computational Design and Directed Evolution" J. Biol. Chem. 2017, 292(8), 3481-3495.
Arnon et al., "The mechanisms controlling the recognition of tumor- and virus-infected cells by NKp46", Blood, Jan. 15, 2004;103(2):664-672.
Arnould et al., "Trastuzumab-based treatment of HER2-positive breast cancer: an antibody-dependent cellular cytotoxicity mechanism?", Br J Cancer, 2006, 94(2):259-267.
Askoxylakis et al., "A New Peptide Ligand for Targeting Human Carbonic Anhydrase IX, Identified through the Phage Display Technology", PLoS ONE, Dec. 2010, 5(12):10 pages.
Augoff et al., "Upregulated expression and activation of membrane-associated proteases in esophageal squamous cell carcinoma." Oncology reports, 2014, 31(6):2820-2826.
Ausiello et al., "Functional topography of discrete domains of human CD38," Tissue Antigens, Dec. 2000, 56(6):539-547.
Baek et al. "Effects of Histidine and Sucrose on the Biophysical Properties of a Monoclonal Antibody," Pharmaceutical Antibody, 2017, 34(3):629-639.
Banerji et al., "A Cancer research UK Phase I/IIA Trail of BT1718 (a first in class Bicycle Drug Conjugate) Given Intravenously in Patients with Advanced Solid Tumours," Journal of Clinical Oncology, Jan. 2018, 36(15):PS2610. (1 Page).
Banerji et al., "Preliminary pharmacokinetic assessment of BT1718: A phase I/IIa trial of BT1718 (a first in class Bicycle Toxin Conjugate) in patients with advanced solid tumours." In european journal of cancer, 2018, 103:E65-e65.
Barbas III et al., "Semisynthetic combinatorial antibody libraries: a chemical solution to the diversity problem," Proceedings of the National Academy of Sciences of the United States of America, May 1992, 89(10):4457-4461.
Barbolina et al., Microenvironmental regulation of membrane type 1 matrix metalloproteinase activity in ovarian carcinoma cells via collagen-induced EGR1 expression. Journal of Biological Chemistry, 2007, 282(7):4924-4931.
Bardia et al., "Efficacy and safety of anti-trop-2 antibody drug conjugate sacituzumab govitecan (IMMU-132) in heavily pre-treated patients with metastatic triple-negative breast cancer." Journal of Clinical Oncology, 2017, 35(19):2141.
Bech et al., "Chemical Strategies for Half-Life Extension of Biopharmaceuticals: Lipidation and Its Alternatives," ACS Medicinal Chemistry Letters, Jun. 2018, 9(7):577-580.
Bennett et al., "Abstract 4481: BT5528, an EphA2-targeting Bicycle Toxin Conjugate (BTC): Profound efficacy without bleeding and coagulation abnormalities in animal models", Cancer Research, 2019, 79(13 suppl):4481. 2 pages.
Bennett et al., "Abstract 5854: BT5528, a Bicycle Toxin Conjugate targeting EphA2 has potent anti-tumor activity without bleeding or coagulation abnormalities in preclinical models." Cancer Res., 2018, 78(13 suppl):5854.
Bennett et al., "Abstract 5855: Bicycle Drug Conjugates Targeting EphA2 for the Treatment of Solid Tumors: Discoverv and Selection of BT5528", Cancer Research, 2018, 78(13 suppl):5855. 2 pages.
Bennett et al., "Development of BT1718, a Bicycle Drug Conjugate® (BDC) targeting MT1-MMP for treatment of solid tumours," European Journal of Cancer, Nov. 2016, 69(1):S21.
Bennett et al., "MMAE Delivery Using the Bicycle Toxin Conjugate BT5528," Mol Cancer Ther., Jul. 2020, 19(7):1385-1394.
Bennett et al., "The Mechanism of Action of BT1718, a Novel Small-Molecule Drug Conjugate for the Treatment of Solid Tumors Expressing MT1-MMP," AAACR-NCI-EOrTC International Conference: Molecular Taroets and Cancer Therapeutics, Jan. 2018, 26-30.
Bennett, "BT1718, a Bicycle Drug Conjugate (BTC): Profound Efficacy Without Bleeding and Coaaulation Abnormalities in Animal Models," AACR Annual Meeting 2019, 4481, 2 pages.
Ben-Shmuel et al., "Unleashing Natural Killer Cells in the Tumor Microenvironment—The Next Generation of Immunotherapy?", Front Immunol., 2020, 11:275.
Berenson, "Multiple Myeloma," Merck Manual, Reterived from :https://www.merckmanuals.com/home/blood-disorders/plasma-cell-disorders/multiplemyeloma?query=multiple%20myeloma, Oct. 2022.
Berge et al., " Pharmaceutical Salts," Journal of Pharmaceutical Sciences, Jan. 1977, 66(1):1-19.
Berkel et al. "Binding of (5 S)-penicilloic acid to penicillin binding protein 3." ACS chemical biology 8, No. 10 (2013): 2112-2116.
Bernhagen et al., "Design, synthesis and characterization of different bicyclic peptides with enhanced binding and selectivity for various integrins", Reterived form : https://ec.europa.eu/research/participants/documents/downloadPublic?documentIds= 080166e5acfd6757&appId=PPGMS, Oct. 14, 2016, XP55622035:1-6.
C36 Beswick, Paul, "Bicycles—An entirely new class of therapeutics," accessed on https://www.bicycletherapeutics.com/wp-content/uploads/RSC-02-May-2019.pdf, 2019, 21 pages.
Bicycle Therapeutics, "Bicycle Therapeutics and Cancer Research UK Announce Inititation of FirstClinical Study of a Bicyclic Peptide (Bicycle®)," Press Release, Feb. 13, 2018, https://investors.bicycletherapeutics.com/node/6651/pdf.
Bicycle Therapeutics, "Bicycle Therapeutics to Present New BT1718 Data in the "New Drugs on the Horizon" Session at the 2018 American Association for Cancer Research Meeting," Press Release. Apr. 3, 2018.
Bicycle Therapeutics, "Bicycle Therapeutics to Present on BT5528, a Bicycle Toxin Conjugate Targeting EphA2 for the Treatment of Solid Tumours, at World ADC 2019," Business Wire Release. Mar. 5, 2019.
BicycleTx Limited, "Study BT5528-100 in Patients With Advanced Solid Tumors Associated With EphA2 Expression," ClinicalTrials.gov Identifier NCT04180371. First Posted Nov. 27, 2019; Accessed Dec. 30, 2022: https://clinicaltrials.gov/ct2/show/NCT04180371.
Bilsky, Mark H., "Gliomas", Merck Manual (https://www.merckmanuals.com/professional/neurologic-disorders/intracranial-and-spinal-tumors/gliomas), May 2023, 8 pages.

(56) References Cited

OTHER PUBLICATIONS

Binda et al., "The EphA2 receptor drives self-renewal and tumorigenicity in stem-like tumor-propagating cells from human glioblastomas," Cancer Cell, Dec. 11, 2012, 22(6):765-780.

Biron et al., "Improving oral bioavailability of peptides by multiple N-methylation: somatostatin analogues," Angewandte Chemie International Edition, 2008, 47(14):2595-2599.

Blank et al., " Absence of Programmed Death Receptor 1 Alters Thymic Development and Enhances Generation of CD4/CD8 Double-Negative TCR-Transgenic T Cells " in Journal of Immunology, Nov. 2003, 171(19):4574-4581.

Bogaerts et al., "Individual patient data analysis to assess modifications to the RECIST criteria." European journal of cancer, 2009, 45(2):248-260.

Bolland et al., "Spontaneous autoimmune disease in Fc(gamma)RIIB-deficient mice results from strain-specific epistasis", Immunity, Aug. 2000, 13(2):277-285.

Booth et al., "Crowd control in the crypt," Nat Med., Dec. 2002, 8(12):1360-1361.

Borghaei et al., "Nivolumab versus docetaxel in advanced nonsquamous non-small-cell lung cancer." New England Journal of Medicine, 2015, 373(17):1627-1639.

Borrelli et al., "Cell Penetrating Peptides as Molecular Carriers for Anti-Cancer Agents," Molecules, Feb. 2018, 23(2):295. (28 pages).

Boruchov et al., "Activating and inhibitory IgG Fc receptors on human DCs mediate opposing functions", The Journal of Clinical Investigation, 2005, 115(10):2914-2923.

Bouchard et al., "Antibody—drug conjugates—a new wave of cancer drugs." Bioorganic & medicinal chemistry letters, 2014, 24(23):5357-5363.

Brahmer et al., "Nivolumab versus docetaxel in advanced squamous-cell non-small-cell lung cancer." New England Journal of Medicine, 2015, 373(2):123-135.

Brannan et al., "EphA2 in the early pathogenesis and progression of non-small cell lung cancer," Cancer Prev Res (Phila)., Dec. 2009, 2(12):1039-1049.

Brantley-Sieders et al., "Eph receptor tyrosine kinases in tumor and tumor microenvironment", Current Pharmaceutical Design, 2004, 10(27):3431-3442.

Brantley-Sieders et al., "Eph/Ephrin Profiling in Human Breast Cancer Reveals Significant Associations between Expression Level and Clinical Outcome", PLOS ONE, 2011, 6(9):e24426.

Brantley-Sieders et al., "Impaired tumor microenvironment in EphA2-deficient mice inhibits tumor angiogenesis and metastatic progression," FASEB J., Nov. 2005, 19(13):1884-1886.

Bristol-Myers Squibb, "An Investigational Immuno-Therapy Study to Investigate the Safety and Effectiveness of Nivolumab, and Nivolumab Combination Therapy in Virus-Associated Tumors—Full Text View—Clinicaltrials." Gov. [(accessed on Jan. 30, 2021)] (2018).

Brown et al., "Blockade of programmed death-1 ligands on dendritic cells enhances T cell activation and cytokine production", Journal of Immunolgy, Feb. 2003, 170(3):1257-1266.

Cabanillas et al., "Phase I study of maytansine using a 3-day schedule," Cancer Treat Rep., Mar. 1978, 62(3):425-428.

Cancer Research UK, "Soft tissue sarcomas," Reterived from http://aboutcancer.cancerresearchuk.org/about-cancer/soft-tissue-sarcoma, Sep. 2022.

Cancer Research UK, "Triple Negative Breast Cancer," Reterived from: https://www.cancerresearchuk.org/about-cancer/breast-cancer/stages-types-grades/types/triplenegative-breast-cancer#, Sep. 2022, 6 pages.

Cancer Research UK, "Types of lung cancer," Reterived form: https://www.cancerresearchuk.org/about-cancer/lung-cancer/stages-types-grades/types#, Sep. 2022.

Cancer Research UK, "Your mouth and cancer drugs," Reterived form : https://www.cancerresearchuk.org/about-cancer/cancer-in-general/treatment/cancer-drugs/sideeffects/your-mouth, Sep. 2022, 5 pages.

Caratelli et al., "FCγChimeric Receptor-Engineered T Cells: Methodology, Advantages, Limitations, and Clinical Relevance", Frontiers in Immunology, Apr. 27, 2017, :8:457, 8 pages.

Centers for Disease Control and Prevention, "What Can I Do to Reduce My Risk of Ovarian Cancer?", Division of Cancer Prevention and Control, Aug. 31, 2022, 1 page.

Chabner et al.,"Initial clinical trials of maytansine, an antitumor plant alkaloid." Cancer Treat Rep., 1978, 62(3):429-433.

Chahinian et al., "Phase I study of weekly maytansine given by iv bolus or 24-hour infusion," Cancer Treat Rep., Nov. 1979, 63(11-12), 1953-1960.

Challita-Eid et al., "Enfortumab Vedotin Antibody-Drug Conjugate Targeting Nectin-4 Is a Highly Potent Therapeutic Agent in Multiple Preclinical Cancer Models", Cancer Research, 2016, 76(10):3003-3013.

Chan and Nie, "Quantum dot bioconjugates for ultrasensitive nonisotopic detection," Science, Sep. 25, 1998; 281(5385):2016-2018.

Chandrasekar, "Bladder Cancer," Merck Manual. ; Reretrieved form: https://www.merckmanuals.com/professional/genitourinary-disorders/genitourinary-cancers/bladder-cancer, Sep. 2022.

Chandrasekar, "Prostate Cancer," Merck Manual. Reterived from: https://www.merckmanuals.com/professional/genitourinary-disorders/genitourinary-cancers/prostate-cancer, Sep. 2022.

Chang et al., "Five different anti-prostate-specific membrane antigen (PSMA) antibodies confirm PSMA expression in tumor-associated neovasculature," Cancer Res., Jul. 1, 1999, 59(13):3192-3198.

Chang et al., "Subtiligase: A Tool for Semisynthesis of Proteins", Proc Natl Acad Sci, 1994, 91(26):12544-12548.

Chemnitz et al., "RNA fingerprints provide direct evidence for the inhibitory role of |TGFβand PD-1 on CD4+ T cells in Hodgkin lymphoma", Blood, 2007, 110(9):3226-3233.

Chen and Harrison, "Cell-Penetrating Peptides in Drug Development: Enabling Intracellular Targets," Biochemical Society Transactions, 2007, 35(4):821-825.

Chen et al., "Association of FCGR3A and FCGR3B copy number variations with systemic lupus erythematosus and rheumatoid arthritis in Taiwanese patients", Arthritis & Rheumatology, 2014, 66(11):3113-3121.

Chen et al., "Structurally diverse cyclisation linkers impose different backbone conformations in bicyclic peptides," Chembiochem., May 7, 2012, 13(7):1032-1038.

Chen et al., "The Bicycle Platform: an Efficient Technology to Generate High Affinity, High Selectivity Molecules (Bicycles®) with Unique Drug Like Properties that are Amenable to Conjugation," URL:https://www.bicycletherapeutics.com/wp-content/uploads/16_PEGS-Bicycle_-30-04-2017-poster.pdf, Apr. 26, 2017, 1 page.

Cheng et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology", J Molecular Diagnostics, 2015, 17(3):251-264.

Cheng et al., "Blockade of EphA receptor tyrosine kinase activation inhibits vascular endothelial cell growth factor-induced angiogenesis," Mol Cancer Res., Nov. 2002, 1(1):2-11.

Cherney et al., "Macrocyclic Amino Carboxylates as Selective MMP-8 Inhibitors," Journal of Medicinal Chemistry, May 1998, 41(11):1749-1751.

Chiche et al., "Hypoxia-inducible carbonic anhydrase IX and XII promote tumor cell growth by counteracting acidosis through the regulation of the intracellular pH," Cancer Res., Jan. 1, 2009, 69(1):358-368.

Chinnery et al., "Viral antigen mediated NKp46 activation of NK cells results in tumor rejection via NK-DC crosstalk", Oncoimmunology, 2012, 1(6):874-883.

Christina Chun, "What are the most curable cancers?", Medical news Today(https://www.medicalnewstoday.com/articles/322700 Accessed May, 8, 2020), 2020, 8 pages.

Chung et al., "Bicycle synthesis through peptide macrocyclization using aziridine aldehydes followed by late stage disulfide bond installation." MedChemComm, 2023, 4(7):1124-1128.

(56) References Cited

OTHER PUBLICATIONS

Clarkson et al., "Treatment of refractory immune thrombocytopeniaurpura with an anti-Fc gamma-receptor antibody", The New England Journal of Medicine, 1986, 314(19):1236-1239.
Claus et al., "Tumor-targeted 4-1BB agonists for combination with T cell bispecific antibodies as off-the-shelf therapy", Sci Transl Med., Jun. 2019, 11(496):eaav5989. (12 Pages).
Clynes et al., "Inhibitory Fc receptors modulate in vivo cytotoxicity against tumor targets", Nature Medicine, Apr. 2000, 6(4):443-446.
Committee for Medicinal Products for Human Use (CHMP), "Assessment Report: Kadcyla; International non-proprietary name: Trastuzumab emtansine; Procedure No. EMEA/H/C/002389/0000," European Medicines Agency. Sep. 19, 2013; EMA/749228/2013.
Connolly et al., "Complexities of TGF-β Targeted Cancer Therapy", Int'l J. Biological Sciences, 2012, 8(7):964-978.
Cook et al., "Pharmacokinetic (PK) Assessment of BT1718: A Phase 1/2a Study of BT1718, a First in Class Bicycle Toxin Conjugate (BTC), in Patients (PTS) with Advanced Solid Tumours," Annals of Oncology 2019; vol. 30, Jan. 2019, Page v174.
Cortes et al., "Phase II study of the halichondrin B analog eribulin mesylate in patients with locally advanced or metastatic breast cancer previously treated with an anthracycline, a taxane, and capecitabine." Journal of Clinical Oncology, 2010, 28(25):3922-3928.
Costello et al., "Defective expression and function of natural killer cell-triggering receptors in patients with acute myeloid leukemia", Blood, 2002, 99(10):3661-3667.
Crameri et al., "Construction and evolution of antibody-phage libraries by DNA shuffling," Nature Medicine, Jan. 1996, 2(1):100-102.
Cui, J. Jean., "A New Challenging and Promising Era of Tyrosine Kinase Inhibitors", ACS Med Chem Lett., 2014, 5(4):272-274.
Curiel et al., "Blockade of B7-H1 improves myeloid dendritic cell-mediated antitumor immunity", In Nature medicine, 2003, 9(5):562-567.
Dagher et al., "c-Kit and CD38 are expressed by long-term reconstituting hematopoietic cells present in the murine yolk sac," Biol Blood Marrow Transplant, 1998, 4(2):69-74.
Davies et al., "Antibody VH Domains as Small Recognition Units," Bio/Technology, May 13, 1995, 13(5):475-479.
Davis et al., "Natural killer cells unleashed: Checkpoint receptor blockade and BiKE/TriKE utilization in NK-mediated anti-tumor immunotherapy", Semin Immunol., 2017, 31:64-75.
Dawson et al., "Synthesis of proteins by native chemical ligation," Science, Nov. 1994, 266(5186):776-779.
De Kruif et al., "Selection and Application of Human Single Chain Fv Antibody Fragments from a Semi-synthetic Phage Antibody Display Library with Designed CDR3 Regions," Journal of Molecular Biology, Apr. 1995, 248(1):97-105.
de la Pena et al., "Expression of the matrix metalloproteases 2, 14, 24, and 25 and tissue inhibitor 3 as potential molecular markers in advanced human gastric cancer." Disease markers 2014 (2014).
Deaglio et al., "CD38 is a signaling molecule in B-cell chronic lymphocytic leukemia cells," Blood, Sep. 15, 2003, 102(6):2146-2155.
Debre et al., "Infusion of Fc gamma fragments for treatment of children with acute immune thrombocytopeniaurpura", Lancet, 1993, 342(8877):945-949.
Derossi et al., "The third helix of the Antennapedia homeodomain translocates through biological membranes," Journal if Biological Chemistry, Apr. 1994, 269(14):10444-10450.
Deyle et al., "Phage Selection of Cyclic Peptides for Application in Research and Drug Development," Accounts of Chemical Research, 2017, 50(8):1866-1874.
Dharmadhikari, et al., "CD137 and CD137L signals are main drivers of type 1, cell-mediated immune responses." Oncoimmunology, 2016, 5(4):e1113367.
Di, "Strategic Approaches to Optimizing Peptide ADME Properties," AAPS J., Jan. 2015, 17(1):134-143.

Diamantis and Banerji, "Antibody-drug conjugates—an emerging class of cancer treatment." British journal of cancer, 2016, 114(4):362-367.
Diaz-Perlas et al., "Branched BBB-shuttle peptides: chemoselective modification of proteins to enhance blood-brain barrier transport," Chemical Science, Sep. 2018, 9(44):8409-8415.
Dong, et al. "Tumor-associated B7-H1 promotes T-cell apoptosis: a potential mechanism of immune evasion", Nature Medicine, 2002, 8(8):793-800.
Dorfman et al., "Programmed death-1 (PD-1) is a marker of germinal center-associated T cells and angioimmunoblastic T-cell lymphoma." The American journal of surgical pathology, Jul. 2006, 30(7):802-810.
Driggers et al., "The exploration of macrocycles for drug discovery—an underexploited structural class," Nature Reviews Drug Discovery, Jul. 2008, 7(7):608-624.
Dubois et al., "New ways to image and target tumour hypoxia and its molecular responses," Radiotherapy and Oncology, Sep. 2015, 116(3):352-357.
Dufort et al., "789: Generation of a Bicycle NK-TICA(™), a novel NK cell engaging molecule to enhance targeted tumor cytotoxicity", Nov. 10, 2021, 9(Suppl 2):A824-A824. URL:https://jitc.bmj.com/contenl/jitc/9/SuppI_2/A824.full.pdf.
Dunne et al., "EphA2 Expression Is a Key Driver of Migration and Invasion and a Poor Prognostic Marker in Colorectal Cancer," Clin Cancer Res., Jan. 1, 2016, 22(1):230-242.
Duong and Rodan, "The role of integrins in osteoclast function," J Bone Miner Metab., 1999, 17(1):1-6.
Eagan et al., "Early clinical study of an intermittent schedule for maytansine (NSC-153858): brief communication." Journal of the National Cancer Institute, 1978, 60(1):93-96.
Eisenhauer et al., "New response evaluation criteria in solid tumours: revised RECIST guideline (version 1.1)." European journal of cancer, 2009, 45(2):228-247.
Ellenrieder et al., "Role of MT-MMPs and MMP-2 in pancreatic cancer progression." International Journal of Cancer, 2000, 85(1):14-20.
Elson-Schwab et al., "Guanidinylated neomycin delivers large, bioactive cargo into cells through a heparan sulfate-dependent pathway." Journal of Biological Chemistry, 2007, 282(18):13585-13591.
Fauriat et al., "Deficient expression of NCR in NK cells from acute myeloid leukemia: Evolution during leukemia treatment and impact of leukemia cells in NCRdull phenotype induction", Blood, 2007, 109(1):323-330.
Fehrenbacher et al., "Atezolizumab versus docetaxel for patients with previously treated non-small-cell lung cancer (POPLAR): a multicentre, open-label, phase 2 randomised controlled trial." The Lancet, 2016, 387(10030):1837-1846.
Felices et al., "Generation of BiKEs and TriKEs to Improve NK Cell-Mediated Targeting of Tumor Cells", Methods Mol Biol., 2016, 1441:333-346.
Felices et al., "Novel CD19-targeted TriKE restores NK cell function and proliferative capacity in CLL", Blood Adv., 2019, 3(6):897-907.
Fiacco et al., "N-Methyl Scanning Mutagenesis Generates Protease-Resistant G Protein Ligands with Improved Affinity and Selectivity," ChemBioChem, Sep. 2008, 9(14):2200-2203.
Figure 3.8 of "Immunobiology: The Immune System in Health and Disease," Garland Science, 2001.
Flaherty et al., "Nonclinical evaluation of GMA161—an antihuman CD16 (FcγRIII) monoclonal antibody for treatment of autoimmune disorders in CD16 transgenic mice", Toxicological Sciences, 2012, 125(1):299-309.
Forsberg, et al., "CD137 plays both pathogenic and protective roles in type 1 diabetes development in NOD mice." The Journal of Immunology, 2017, 198(10):3857-3868.
Francis et al., "Bone and Soft Tissue Sarcomas: UK Incidence and Survival: 1996-2010," NationalCancer Intelligence Network, Nov. 2013, v2.0.
Fumet et al. "Phase Ib/II trial evaluating the safety, tolerability and immunological activity of durvalumab (MEDI4736)(anti-PD-L1)

(56) References Cited

OTHER PUBLICATIONS plus tremelimumab (anti-CTLA-4) combined with FOLFOX in patients with metastatic colorectal cancer." ESMO open, 2018, 3(4):e000375.

Funaro et al., "Human CD38 is associated to distinct molecules which mediate transmembrane signaling in different lineages." European journal of immunology, Oct. 1993, 23(10):2407-2411.

Funaro et al., "Involvement of the multilineage CD38 molecule in a unique pathway of cell activation and proliferation," J Immunol., Oct. 1990, 145(8):2390-2396.

Galsky et al., "Phase I trial of the prostate-specific membrane antigen-directed immunoconjugate MLN2704 in patients with progressive metastatic castration-resistant prostate cancer." Journal of clinical oncology, 2008, 26(13):2147-2154.

Gandhi et al., "MP69-11 Carbonic Anhydrase IX Assay: A Paradigm Shift in Diagnosis of Malignant Cystic Renal Lesions," J Urol., May 18, 2015, 193(4S):e870-e871.

Garcia-Iglesias et al., "Low NKp30, NKp46 and NKG2D expression and reduced cytotoxic activity on NK cells in cervical cancer and precursor lesions", BMC Cancer, Jun. 16, 2009, 9:186, 8 pages.

Gauthier et al., "Multifunctional Natural Killer Cell Engagers Targeting NKp46 Trigger Protective Tumor Immunity", Cell, 2019, 177(7):1701-1713.

Gelb et al., "Abstract 391: Molecular-based enrichment strategy for Nectin-4 targeted Bicycle toxin conjugate BT8009," Cancer Res., Jul. 1, 2021, 81(13 suppl):391 (poster).

Gelb et al., "Abstract A047: MT1-MMP Immunohistochemistry (IHC) analysis of tumor microarrays(TMAs) using a novel scoring system guides patient selection for BT1718 expansion cohorts," In Molecular Cancer Therapeutics, 2019, 18(12_Suppl):A047.

Gen path diagnostics, "Solid Tumors", Accessed on https://genpathdiagnostics.com/patients/oncology/solid-tumors/, Jun. 30, 2023, 4 pages.

Gentilucci et al., "Chemical Modifications Designed to Improve Peptide Stability: Incorporation of Non-Natural Amino Acids, Pseudo-Peptide Bonds, and Cyclization," Current Pharmacetical Design, 2010, 16(28):3185-3203.

Gfeller et al., "Current tools for predicting cancer-specific T cell immunity," Oncoimmunology, 2016, 5(7):e1177691.

Gleason et al., "CD16xCD33 bispecific killer cell engager (BiKE) activates NK cells against primary MDS and MDSC CD33+ targets", Blood, 2014, 123(19):3016-3026.

Gokel et al., "Crown Ethers: Sensors for Ions and Molecular Scaffolds for Materials and Biological Models," Chem. Rev., 2004, 104(5):2723-2750.

Gradishar et al., "Significantly longer progression-free survival with nab-paclitaxel compared with docetaxel as first-line therapy for metastatic breast cancer." J Clin Oncol., 2009, 27(22):3611-3619.

Gresh, "Neuroblastoma," Merck Manual., Reterived form : https://www.msdmanuals.com/en-in/professional/pediatrics/pediatric-cancers/neuroblastoma, Sep. 2022, 4 pages.

Griffiths et al., "Isolation of high affinity human antibodies directly from large synthetic repertoires," EMBO Journal, Jul. 1994, 13(14):3245-3260.

Grisold et al., "Peripheral neuropathies from chemotherapeutics and targeted agents: diagnosis, treatment, and prevention." Neuro-oncology, 2012, 14(suppl_4):iv45-iv54.

Gu et al., "The influence of the penetrating peptide iRGD on the effect of paclitaxel-loaded MT1-AF7p-conjugated nanoparticles on glioma cells." Biomaterials, 2013, 34(21):5138-5148.

Guo et al., "Prognostic significance of combinations of RNA-dependent protein kinase and EphA2 biomarkers for NSCLC," J Thorac Oncol., Mar. 2013, 8(3):301-308.

Gupta et al., "Intracellular delivery of large molecules and small particles by cell-penetrating proteins and peptides," Advanced Drug Delivery Reviews, Feb. 2005, 57(4):637-651.

Hamanishi et al. "Programmed cell death 1 ligand 1 and tumor-infiltrating CD8+ T lymphocytes are prognostic factors of human ovarian cancer", Proc. Natl. Acad. Sci. USA, 2007, 104(9):3360-3365.

Han et al., "Altered NKp30, NKp46, NKG2D, and DNAM-1 Expression on Circulating NK Cells Is Associated with Tumor Progression in Human Gastric Cancer", Journal of Immunology Research, Sep. 3, 2018, 2018:6248590, 10 pages.

Hanna et al., "Randomized phase III trial of pemetrexed versus docetaxel in patients with non-small-cell lung cancer previously treated with chemotherapy." Journal of clinical oncology, 2004, 22(9):1589-1597.

Harrison et al., "Abstract 5144: BT1718, a novel bicyclic peptide-maytansinoid conjugate targeting MT1-MMP for the treatment of solid tumors: Design of bicyclic peptide and linker selection," Cancer Res., 2017, 77(13 suppl):5144.

Hart, et al., "De novo identification of lipid II binding lipopeptides with antibacterial against vancomycin-resistant bacteria." Chemical Science, 2017, 8(12):7991-7997.

Hart, et al., "Cell binding and internalization by filamentous phage displaying a cyclic Arg-Gly-Aspcontaining peptide", J. Biol. Chem., 1994, 269:12468-12474.

Hasmim et al., "Critical Role of Tumor Microenvironment in Shaping NK Cell Functions: Implication of Hypoxic Stress", Frontiers in Immunology, Sep. 23, 2015, 6:482, 9 pages.

He et al., "Matrix metalloproteinase-14 is a negative prognostic marker for patients with gastric cancer." Digestive diseases and sciences, 2013, 58:1264-1270.

Helft et al., "A phase I study of cantuzumab mertansine administered as a single intravenous infusion once weekly in patients with advanced solid tumors." Clinical cancer research, 2004, 10(13):4363-4368.

Henriques et al., "Functional characterization of peripheral blood dendritic cells and monocytes in systemic lupus erythematosus", Rheumatology International, Apr. 2012, 32(4):863-869.

Herbst et al., "Pembrolizumab versus docetaxel for previously treated, PD-L 1-positive, advanced non-small-cell lung cancer (KEY-NOTE-010): a randomised controlled tria", Lancet, Apr. 2016, 387(10027):1540-1550.

Hershman, "Thyroid Cancers," Merck Manual, Reterived from : https://www.merckmanuals.com/professional/endocrine-and-metabolic-disorders/thyroid-disorders/thyroid-cancers, Sep. 2020.

Hess et al., "Backbone Cyclic Peptidomimetic Melanocortin-4 Receptor Agonist as a Novel Orally Administrated Drug Lead for Treating Obesity," Journal of Medicinal Chemistry, Jan. 26, 2008, 51(4):1026-1034.

Hess et al., "Molecular Regulation of Tumor Cell Vasculogenic Mimicry by Tyrosine Phosphorylation: Role of Epithelial Cell Kinase (Eck/EphA2", Cancer Research, 2001, 61(8):3250-3255.

Hikari et al., "Tags for labeling protein N-termini with subtiligase for proteomics", Bioorganic & Medicinal Chemistry Letters, Nov. 2008, 18 (22):6000-6003.

Hill et al: "Constraining Cyclic Peptides To Mimic Protein Structure Motifs", Angewandte Chemie International Edition, Nov. 24, 2014, 53(48):13020-13041.

Hinner et al., "Tumor-Localized Costimulatory T-Cell Engagement by the 4-1BB/HER2 Bispecific Antibody-Anticalin Fusion PRS-343", Clinical Cancer Research Oct. 2019, 23(19):5878-5889.

Hirano et al. "Blockade of B7-H1 and PD-1 by monoclonal antibodies potentiates cancer therapeutic immunity," Cancer Research, 2005, 65(3):1089-1096.

Hoogenboom et al., "By-passing immunisation. Human antibodies from synthetic repertoires of germline VH gene segments rearranged in vitro," Journal of Molecular Biology, Sep. 1992, 227(2):381-388.

Hoshino et al., "Mapping of the catalytic and epitopic sites of human CD38/NAD+ glycohydrolase to a functional domain in the carboxvl terminus," J Immunol., Jan. 15, 1997, 158(2):741-747.

Hsu et al., "Efficacy of plasmin-treated intravenous gamma-globulin for therapy of Kawasaki syndrome", The Pediatric Infectious Disease Journal, Jun. 1993, 12(6):509-512.

Hu-Lieskovan and Ribas, "New Combination Strategies Using Programmed Cell Death 1/Programmed Cell Death Ligand 1 Checkpoint Inhibitors as a Backbone," Cancer J., Jan./Feb. 2017, 23(1):10-22.

Hurov et al., "BT7480, a novel fully synthetic tumor-targeted immune cell agonist (TICA™) induces tumor localized CD137

(56) References Cited

OTHER PUBLICATIONS agonism", Retrieved from the Internet: URL: https://www.bicycletherapeutics.com/wp-content/uploads/2020-06-16-BT7480-AACR-2020-poster-P5552_Final_CD137-in-title-002.pdf, Jun. 20, 2020, 1 page.
Ide et al., "A novel method for artificial lipid-bilayer formation," Biosensors and Bioelectronics, 2005, 21(4):672-677.
Inman et al., "PD-L1 (B7-H1) expression by urothelial carcinoma of the bladder and BCG-induced granulomata: associations with localized stage progression", Cancer, 2007, 109(8):1499-1505.
Ip et al., "Atypical localization of membrane type 1-matrix metalloproteinase in the nucleus is associated with aggressive features of hepatocellular carcinoma." Molecular Carcinogenesis: Published in cooperation with the University of Texas MD Anderson Cancer Center, 2007, 46(3):225-230.
Izawa et al., "$H_2O_2$ production within tumor microenvironment inversely correlated with infiltration of CD56(dim) NK cells in gastric and esophageal cancer: possible mechanisms of NK cell dysfunction", Cancer Immunology, Immunotherapy, 2011, 60(12):1801-1810.
Jackson and Stover, "Using the lessons learned from the clinic to improve the preclinical development of antibody drug conjugates." Pharmaceutical research, 2015, 32(11):3458-3469.
Jackson et al., "A human antibody-drug conjugate targeting EphA2 inhibits tumor growth in vivo", Cancer Research, Nov. 15, 2008, 68(22):9367-9374.
Jespers et al., "Selection of optical biosensors from chemisynthetic antibody libraries," Protein Engineering, Design and Selection, Oct. 2004, 17(10):709-713.
Jin et al., "αVβ3 Integrin-Targeted Radionuclide Therapy with 64Cu-cyclam-RAFT-c(-RGDfK-)4," Mol Cancer Ther., Sep. 2016, 15(9):2076-2085.
Johnson et al., "Melanoma-specific MHC-II expression represents a tumour-autonomous phenotype and predicts response to anti-PD-1/PD-L1 therapy", Nature Communications, Jan. 29, 2016, 7:10582(10 pages).
Johnson et al., "Relationships between drug activity in NCI preclinical in vitro and in vivo models and early clinical trials," British Journal of Cancer, 2001, 84(10):1424-1431.
Jones et al., "Randomized phase III study of docetaxel compared with paclitaxel in metastatic breast cancer." Journal of Clinical Oncology, 2005, 23(24):5542-5551.
Jones et al., "Targeting membrane proteins for antibody discovery using phage display," Scientific Reports, May 18, 2016, 6(1):1-11.
Kamat et al., "The clinical relevance of stromal matrix metalloproteinase expression in ovarian cancer." Clinical Cancer Research, 2006, 12(6):1707-1714.
Kamijo et al., "Aberrant CD137 ligand expression induced by GATA6 overexpression promotes tumor progression in cutaneous T-cell lymphoma." Blood, The Journal of the American Society of Hematology, 2018, 132(18):1922-1935.
Kanazawa et al., "Non-obese-diabetic mice: immune mechanisms of pancreatic β-cell destruction," Diabetologia, 1984, 27:113-115.
Kang et al., "A randomized, open-label, multicenter, adaptive phase 2/3 study of trastuzumab emtansine (T-DM1) versus a taxane (TAX) in patients (pts) with previously treated HER2-positive locally advanced or metastatic gastric/gastroesophageal junction adenocarcinoma (LA/MGC/GEJC)." (2016): 5-5.
Kang, et al., "Anti-CD137 suppresses tumor growth by blocking reverse signaling by CD137 ligand." Cancer research, 2017, 77(21):5989-6000.
Keith, "Lung Carcinoma," Merck Manual, Reterived on: https://www.merckmanuals.com/professional/pulmonary-disorders/tumors-of-the-lungs/lung-carcinoma, Sep. 2021, 18 pages.
Kell, Douglas B., "The Transporter-Mediated Cellular Uptake and Efflux of Pharmaceutical Drugs and Biotechnology Projects: How and Why Phospholipid Bilayer Transport is Negligible in Real Biomembranes," Molecules, 2021, 26(5629):40 pages.

Kellog et al., "Disulfide-linked antibody—maytansinoid conjugates: Optimization of in vivo activity by varying the steric hindrance at carbon atoms adjacent to the disulfide linkage." Bioconjugate chemistry, 2011, 22(4):717-727.
Kemp and McNamara, "Conformationally restricted cyclic nonapeptides derived from L-cysteine and LL-3-amino-2-piperidone-6-carboxylic acid (LL-Acp), a potent .beta.-turn-inducing dipeptide analog." J. Org. Chem., 1985, 50(26):5834-5838.
Kerkela et al., "Differential patterns of stromelysin-2 (MMP-10) and MT1-MMP (MMP-14) expression in epithelial skin cancers." British journal of cancer, 2001, 84(5):659-669.
Kessenbrock et al., "Matrix metalloproteinases: regulators of the tumor microenvironment." Cell, 2010, 141(1):52-67.
Khan et al., "Engineering Lipid Bilayer Membranes for Protein Studies," International Journal of Molecular Sciences, Nov. 2013, 14(11):21561-21597.
Kikuchi et al., "Immunohistochemical detection of membrane-type-1-matrix metalloproteinase in colorectal carcinoma." British journal of cancer, 2000, 83(2):215-218.
Kim et al., "Synergistic signals for natural cytotoxicity are required to overcome inhibition by c-Cbl ubiquitin ligase", Immunity, Feb. 26, 2010, 32(2):175-186.
Kim, et al., "Reverse signaling through the costimulatory ligand CD137L in epithelial cells is essential for natural killer cell-mediated acute tissue inflammation." Proceedings of the National Academy of Sciences, 2012, 109(1): E13-E22.
Kinch et al., "Predictive Value of the EphA2 Receptor Tyrosine Kinase in Lung Cancer Recurrence and Survival", Clin Cancer Res., 2003, 9(2):613-618.
Kitanaka et al., "CD38 ligation in human B cell progenitors triggers tyrosine phosphory lation of CD19 and association of CD19 with lyn and phosphatidylinositol 3-kinase," J Immunol., 1997, 159(1):184-192.
Kitanaka et al., "CD38-mediated signaling events in murine pro-B cells expressing human CD38 with or without its cytoplasmic domain," J Immunol., Feb. 15, 1999, 162(4):1952-1958.
Kleinau et al., "Induction and suppression of collagen-induced arthritis is dependent on distinct fcgamma receptors", J Exp Med., May 2000, 191(9):1611-1616.
Knight et al., "Three genes for lupus nephritis in NZB x NZW mice," Journal of Experimental Medicine, Jun. 1978, 147(6):1653-1660.
Konishi et al., "B7-H1 Expression on Non-Small Cell Lung Cancer Cells and Its Relationship with Tumor-Infiltrating Lymphocytes and Their PD-1 Expression", Clin Cancer Res., 2004, 10(15):5094-5100.
Konopleva et al., "Ligation of cell surface CD38 protein with agonistic monoclonal antibody induces a cell growth signal in myeloid leukemia cells," J Immunol., Nov. 1, 1998, 161(9):4702-4708.
Koo et al., "Reduction of the CD16-CD56bright NK Cell Subset Precedes NK Cell Dysfunction in Prostate Cancer", PLoS One, 2013, 8(11):e78049, 8 pages.
Kreidieh et al., "Overview, prevention and management of chemotherapy extravasation." World journal of clinical oncology, 2016, 7(1):87.
Krishnamoorthy et al., "Breaking the Permeability Barrier of *Escherichia coli* by Controlled Hyperporination of the Outer Membrane." Antimicrob Agents Chemother, 2016, 60(12):7372-7381.
Krop et al., "Trastuzumab emtansine versus treatment of physician's choice for pretreated HER2-positive advanced breast cancer (TH3RESA): a randomised, open-label, phase 3 trial." The Lancet Oncology, 2014, 15(7): 689-699.
Kumagai et al., "Ligation of CD38 suppresses human B lymphopoiesis," J Exp Med., Mar. 1, 1995, 181(3):1101-1110.
Kylväjä, et al., "Penicillin binding protein 3 of *Staphylococcus aureus* NCTC 8325-4 binds and activates human plasminogen." BMC research notes, 2016, 9:1-10.
Landolt et al., "Clear cell renal cell carcinoma is linked to epithelial-to-mesenchymal transition and to fibrosis." Physiological reports, 2017, 5(11):e13305.
Lani et al., "Identification of high affinity, highly selective bicyclic peptides (Bicycles®) to transmembrane proteins using phage dis-

(56) References Cited

OTHER PUBLICATIONS play screening on whole cells," Abstract, PEGS Summit, Boston, Massachusetts, May 2017, 1 page.
Lanman et al., "Analytical and Clinical Validation of a Digital Sequencing Panel for |Quantitative, Highly Accurate Evaluation of Cell-Free Circulating Tumor Dna", PLoS One, 2015, 10(10):e0140712.
Laudanski et al., "Increased serum level of membrane type 1-matrix metalloproteinase (MT1-MMP/MMP-14) in patients with breast cancer." Folia histochemica et cytobiologica, 2010, 48(1):101-103.
Lea and Simeonov, "Fluorescence polarization assays in small molecule screening," Expert Opinion in Drug Discovery, Jan. 2011, 6(1):17-32.
Lee and Aarhus, "ADP-ribosyl cyclase: an enzyme that cyclizes NAD+ into a calcium-mobilizing metabolite," Cell Regul., Mar. 1991, 2(3):203-209.
Lee et al., "ADP-ribosyl cyclase and CD38. Multi-functional enzymes in Ca+2 signaling," Adv Exp Med Biol., 1997, 419:411-419.
Lee et al., "Structural determination of a cyclic metabolite of NAD+ with intracellular Ca2+-mobilizing activity," J Biol Chem., Jan. 25, 1989, 264(3):1608-1615.
Leighton, "Pharmacology Review: Kadcyla (ado-trastuzumab emtansine)," In Center for Drug Evaluation and Research Application No. 1254270rio 1 sOOO., Feb. 2020.
Levi et al., "Characterization of tumor infiltrating Natural Killer cell subset", Oncotarget, May 30, 2015, 6(15):13835-13843.
Levine et al. "Methionine residues as endogenous antioxidants in proteins", PNAS, 1996, 93(26):15036-15040.
Li et al., "Fluorescent Mu selective opioid ligands from a mixture based cyclic peptide library." ACS combinatorial science, 2012, 14(12):673-679.
Li et al., "Targeting the Fc receptor in autoimmune disease", Expert Opinion on Therapeutic Targets, 2014, 18(3):335-350.
Li et al., "The overexpression membrane type 1 matrix metalloproteinase is associated with the progression and prognosis in breast cancer." American Journal of Translational Research, 2015, 7(1):120.
Li et al., "Up-regulation of EphA2 and down-regulation of EphrinA1 are associated with the aggressive phenotype and poor prognosis of malignant glioma", Tomor Biology, 2010, 31(5):477-488.
Li, et al., "A novel strategy for in vitro selection of peptide-drug conjugates." Chemistry & biology, 2003, 10(3):233-239.
Li, et al., "Increasing the antimicrobial activity of nisin-based lantibiotics against Gram-negative pathogens." Applied and environmental microbiology, 2018, 84(12):e00052-18.
Lian at al, Screening Bicyclic Peptide Libraries for Protein-Protein Interaction Inhibitors: Discovery of Journal of the American Chemical Society, Aug. 14, 2013, 135(32):11990-11995.
Lian et al., "Cell-Permeable Bicyclic Peptide Inhibitors against Intracellular Proteins", Journal of the American Chemical Society, Jul. 2014, 136(28):9830-9833.
Lin et al., "EphA2 overexpression is associated with angiogenesis in ovarian cancer," Cancer, Jan. 15, 2007, 109(2):332-340.
Linch et al., "OX40 Agonists and Combination Immunotherapy: Putting the Pedal to the Metal," Frontiers in Oncology, Feb. 16, 2015, 5(34):1-14.
Linde et al., "Structure-Activity Relationship and Metabolic Stability Studies of Backbone Cyclization and N-Methylation of Melanocortin Peptides," Biopolymers, 2008, 90(5):671-682.
Lindstrom et al., "Myasthenia gravis," Advances in Immunology, Dec. 1988, 42:233-284.
Liu et al., "Abstract 3642: Tumor-antigen expression-dependent activation of the CD137 costimulatory pathway by bispecific DART proteins," American Association for Cancer Research, Jul. 2017, 77(supp 13):1-4.
Liu et al., "Plasma cells from multiple myeloma patients express B7-H1 (PD-L1) and increase expression after stimulation with IFN-{ gamma} and TLR ligands via a MyD88-, TRAF6-, and MEK-dependent pathway", Blood, 2007, 110(1):296-304.
Loktev et al., "Multicyclic Peptides as Scaffolds for the Development of Tumor Targeting Agents," Current Medicinal Chemistry, 2017, 24(999):2141-2155.
Lopus, Manu. "Antibody-DM1 conjugates as cancer therapeutics." Cancer letters, 2011, 307(2):113-118.
Lovering et al. "Escape from flatland: increasing saturation as an approach to improving clinical success." Journal of medicinal chemistry, 2009, 52(21):6752-6756.
Lovering, "Escape from Flatland 2: complexity and promiscuity," Meducinal Chemistry Communication, Dec. 2012, 4(3):515-519.
Lund et al., "CD38 signaling in B lymphocytes is controlled by its ectodomain but occurs independently of enzymatically generated ADP-ribose or cyclic ADP-ribose," J Immunol., Mar. 1, 1999, 162(5):2693-2702.
M.D. Anderson Cancer Center, "Nivolumab and HPV-16 Vaccination in Patients With HPV-16 Positive Incurable Solid Tumors," In ClinicalTrials.gov Identifier NCT02426892. Retreived form https://clinicaltrials.gov/ct2/show/study/NCT02426892, 2015.
MacFarlane 4th et al., "NK cell dysfunction in chronic lymphocytic leukemia is associated with loss of the mature cells expressing inhibitory killer cell Ig-like receptors", Oncoimmunology, May 19, 2017, 6(7):e1330235.
Macheboeuf et al., "Penicillin binding proteins: key players in bacterial cell cycle and drug resistance processes", FEMS Microbiol Rev., 2006, 30(5):673-691.
Mallone et al., "Signaling through CD38 induces NK cell activation," Int Immunol., Apr. 1, 2001, 13(4):397-409.
Mamessier et al., "Human breast tumor cells induce self-tolerance mechanisms to avoid NKG2D-mediated and DNAM-mediated NK cell recognition", Cancer Res., 2011, 71(21):6621-6632.
Manches et al., " In vitro mechanisms of action of rituximab on primary non-Hodgkin lymphomas", Blood, 2003, 101(3):949-954.
Mark, "Renal Cell Carcinoma," Merck Manual , Reterived form https://www.merckmanuals.com/home/kidney-and-urinary-tract-disorders/cancers-of-the-kidney-and-genitourinary-tract/kidney-cancer, Sep. 2021.
Marks et al., "By-passing immunization. Human antibodies from V-gene libraries displayed on phage," Journal of Molecular Biology, Dec. 1991, 222(3):581-597.
Marme, "VEGFs, angiopoietins, Ephrins and their receptors: putative targets for tumor therapy?" Ann Hematol., 2002, 81(Suppl 2):S66.
Maron et al., "H-2K mutation controls immune response phenotype of autoimmune thyroiditis. Critical expression of mutant gene product in both thymus and thyroid glands," Journal of Experimental Medicine, Oct. 1980, 152(4):1115-1120.
McFarlin et al., "Experimental Allergic Encephalomyelitis in the Rat: Response to Encephalitogenic Proteins and Peptides," Science, Feb. 1973, 179(4072):478-480.
Merck Manual (https://www.merckanuals.com/home/blood-disorders/plasma-celldisorders/multiple-myeloma?q uery=pancreaticu ltiple%20myeloma accessed Apr. 9, 2021).
Merritt et al., "Analysis of EphA2 expression and mutant p53 in ovarian carcinoma," Cancer Biol Ther., Oct. 2006, 5(10):1357-1360.
Michel, et al., "Expression of soluble CD137 correlates with activation-induced cell death of lymphocytes." Cytokine, 2000, 12(6):742-746.
Milowsky et al., Phase 1/2 multiple ascending dose trial of the prostate-specific membrane antigen-targeted antibody drug conjugate MLN2704 in metastatic castration-resistant prostate cancer. In Urologic Oncology: Seminars and Original Investigations, 2016, 34(12):530-e15.
Mitra et al., "Structure—Activity Relationship Analysis of Peptides Targeting the EphA2 Receptor," Biochemistry, 2010, 49(31):6687-6695.
Mittler, el al., "Anti-CD137 antibodies in the treatment of autoimmune disease and cancer." Immunologic research, 2004, 29:197-208.
Miyoshi and Takai, "Nectin and nectin-like molecules: biology and pathology," Am J Nephrol., 2007, 27(6):590-604.

(56) References Cited

OTHER PUBLICATIONS

Mohammad et al., Prognostic value of membrane type 1 and 2 matrix metalloproteinase expression and gelatinase A activity in bladder cancer. The International journal of biological markers, 2010, 25(2):69-74.
Moore et al., "A novel bispecific antibody format enables simultaneous bivalent and monovalent co-engagement of distinct target antigens", Mabs, 2011, 3(6):546-557.
Moraes et al., "Immune checkpoint inhibitors (anti PD-1 or anti PD-L1) versus chemotherapy for second- or third-line treatment of metastatic non-small cell lung cancer," Cochrane Database Syst Rev., 2017, 2017(4):CD012644.
Moretta et al., "Surface NK receptors and their ligands on tumor cells", Seminars in Immunology, 2006, 18(3):151-158.
Morgan et al., "FcgammaRIIIA-158V and rheumatoid arthritis: a confirmation study", Rheumatology (Oxford), 2003, 42(4):528-533.
Morra et al., "CD38 is functionally dependent on the TCR/CD3 complex in human T cells," FASEB J., May 1998, 12(7):581-592.
Morrison, "Chemical Strategies for Bicyclic Peptide Formation," Univ. of Leeds, Sep. 2015, pp. 1-60.
Mudali et al., "Patterns of EphA2 protein expression in primary and metastatic pancreatic carcinoma and correlation with genetic status", Clinical & Experimental Metastasis, 2006, 23(7-8):357-365.
Mudd et al., "Identification and Optimization of EphA2-Selective Bicycles for the Delivery of Cytotoxic Payloads," J Med Chem., 2020, 63(8):4107-4116.
Mugera and Ward, "Acute toxicity of maytansine in F344 rats." Cancer Treatment Reports, 1977, 61(7):1333-1338.
Mulder et al., "Scaffold Optimization in Discontinuous Epitope Containing Protein Mimics of gp120 Using Smart Libraries," Org. Biomol. Chem., 2013, 11:2676-2684.
Mullis et al., "Specific synthesis of DNA in vitro via a polymerase-catalyzed chain reaction," Methods in Enzymology, Jan. 1987, 155:335-350.
Muta et al., "A 13-amino-acid motif in the cytoplasmic domain of Fc gamma RIIB modulates B-cell receptor signalling", Nature, Mar. 3, 1994, 368(6466):70-73.
Nabbe et al., "Coordinate expression of activating Fc gamma receptors I and III and inhibiting Fc gamma receptor type II in the determination of joint inflammation and cartilage destruction during immune complex-mediated arthritis", Arthritis & Rheumatology, Jan. 2003, 48(1):255-265.
Nair et al., "Mimicry of Native Peptide Antigens by the Corresponding Retro-Inverso Analogs is Dependent on Their Intrinsic Structure and Interaction Propensities," The Journal of Immunology, 2003, 170(3):1362-1373.
Nakamoto and Bergemann, "Diverse roles for the Eph family of receptor tyrosine kinases in carcinogenesis," Microsc Res Tech., Oct. 2002, 59(1):58-67.
Nakamura et al., "EPHA2/EFNA1 expression in human gastric cancer", Cancer Science, Jan. 2005, 96(1):42-47.
Nakamura et al., "Involvement of alpha(v)beta3 integrins in osteoclast function," J Bone Miner Metab., 2007, 25(6):337-344.
Nakanishi et al., "Overexpression of B7-H1 (PD-L1) significantly associates with tumor grade and postoperative prognosis in human urothelial cancers" Cancer Immunology, Immunotherapy, 2007, 56:1173-1182.
Nam et. al., "The therapeutic potential of 4-1BB (CD137) in cancer", Current cancer drug targets, 2005, 5(5):357-363.
Nan et al., "Dual function glutamate-related ligands: discovery of a novel, potent inhibitor of glutamate carboxypeptidase II possessing mGluR3 agonist activity," J Med Chem., Mar. 9, 2000, 43(5):772-774.
National cancer institute, "Cancer prevention overview", (https://www.cancer.gov/about-cancer/causes-prevention/patient-prevention-overview-pdq accessed May 8, 2020), 2020, 12 pages.
National Cancer Institute, "What is Cancer", (https://www.cancer.gov/about-cancer/understanding/what-is-cancer, accessed Apr. 9, 2021), 10 pages.
National Cancer Institute, Understanding Cancer and Related Topics, (https://www.cancer.gov/about-cancer/understanding/what-is-cancer, accessed Apr. 9, 2021).
Nayyar et al., "Overcoming Resistance to Natural Killer Cell Based Immunotherapies for Solid Tumors", Feb. 11, 2019 ;9:51, 28 pages.
Neri and Supuran, "Interfering with pH regulation in tumours as a therapeutic strategy," Nature Review Drug Discovery, Sep. 2011, 10(10):767-777.
Nestor et al., "The Medicinal Chemistry of Peptides," Curr. Medicinal Chem, 2009, 16(33):4399-4418.
Nguyen, "Colorectal Cancer," Merck Manual, Retreived from https://www.merckmanuals.com/professional/gastrointestinal-disorders/tumors-of-the-gastrointestinal-tract/colorectal-cancer, 2021.
Nguyen, "Pancreatic Cancer", Merck Manual (https://merckmanuals.com/professional/gastrointestinal-disorders/tumors-of-the-gastrointestinal-tract/pancreatic-cancer?query=adenocarcinomas), Sep. 2022, 4 pages.
NIH National Human Genome Research Institute, "Animal Model," Genome.gov., Jan. 4, 2022.
Nishiwada et al., "Nectin-4 expression contributes to tumor proliferation, angiogenesis and patient prognosis in human pancreatic cancer," Journal of Experimental & Clinical Cancer Research, 2015, 34(1):30. (9 pages.)
Nissim et al., "Antibody fragments from a 'single pot' phage display library as immunochemical reagents," EMBO Journal, Feb. 1994, 13(3):692-698.
Nomi et al., "Clinical Significance and Therapeutic Potential of the Programmed Death-1 Ligand/Programmed Death-1 Pathway in Human Pancreatic Cancer", Clin Cancer Res., 2007, 13(7): 2151-2157.
Oehlke et al., "Cellular uptake of an alpha-helical amphipathic model peptide with the potential to deliver polar compounds into the cell interior non-endocytically," Biochimica et Biophysica Acta, Nov. 1998, 1414(1-2):127-139.
Okazaki et al., "A Rheostat for Immune Responses: the Unique Properties of PD-1 and Their Advantages for Clinical Application," Nat. Immunol., 2013, 14(12):1212-1218.
Okuyama et al., "Small-molecule mimics of an a-helix for efficient transport of proteins into cells," Nature Methods, Feb. 2007, 4(2):153-159.
Oliver et al., "Mouse CD38 is down-regulated on germinal center B cells and mature plasma cells," J Immunol., Feb. 1997, 158(3):1108-1115.
Ortiz et al., "Elucidating the interplay between IgG-Fc valency and FcγR activation for the design of immune complex inhibitors", Science Translational Medicine, Nov. 2016, 8(365):365ra158.
Pahwa et al., "Monitoring and inhibiting MT1-MMP during cancer initiation and progression." Cancers, 2014, 6(1):416-435.
Partida-Sanchez et al., "Cyclic ADP-ribose production by CD38 regulates intracellular calcium release, extracellular calcium influx and chemotaxis in neutrophils and is required for bacterial clearance in vivo," Nat Med., Nov. 2001, 7(11):1209-1216.
Partida-Sanchez et al., "Regulation of dendritic cell trafficking by the ADP-ribosyl cyclase CD38: impact on the development of humoral immunity," Immunity, Mar. 2004, 20(3):279-291.
Pasero et al., "Highly effective NK cells are associated with good prognosis in patients with metastatic prostate cancer", Oncotarget 6(16), Jun. 10, 2015, 14360-14373.
Pavlidou et al., "Nanodiscs Allow Phage Display Selection for Ligands to Non-Linear Epitopes on Membrane Proteins," PLoS One, Article No. e72272, Sep. 2013, 8(9):8 pages.
Pavlova et al., "A role for PVRL4-driven cell-cell interactions in tumorigenesis," Elife., Apr. 30, 2013, 2:e00358, 24 pages.
Pearson et al., "High-Level Clonal FGFR Amplification and Response to FGFR Inhibition in a Translational Clinical Trial", Cancer Discovery, 2016, 6(8):838-851.
Peng et al.,Combined features based on MT1-MMP expression, CD11b+ immunocytes density and LNR predict clinical outcomes of gastric cancer. Journal of translational medicine, 2013, 11(1):1-11.
Phichith, et al., "Novel peptide inhibiting both TEM-1 β-lactamase and penicillin-binding proteins." The FEBS Journal, 2010, 277(23):4965-4972.

(56) References Cited

OTHER PUBLICATIONS

Pickens et al., "Practical Considerations, Challenges and Limitations of Bioconjugation via Azide—Alkyne Cycloaddition," Bioconjugate Chem., 2018, 29:686-701.
Pietraszek et al., "Lumican: a new inhibitor of matrix metalloproteinase-14 activity," FEBS Lett., Nov. 28, 2014, 588(23):4319-4324.
Pivot et al., "Pooled analyses of eribulin in metastatic breast cancer patients with at least one prior chemotherapy." Annals of Oncology, 2016, 27(8):1525-1531.
Platonova et al., "Profound coordinated alterations of intratumoral NK cell phenotype and function in lung carcinoma", Cancer Res., 2011, 71(16):5412-5422.
Polakis, "Antibody Drug Conjugates for Cancer Therapy," Pharmacol Rev., Jan. 2016, 68(1):3-19.
Poliakov et al., "Diverse roles of eph receptors and ephrins in the regulation of cell migration and tissue assembly", Developmental Cell, Oct. 2004;7(4):465-480.
Poon et al., Preclinical safety profile of trastuzumab emtansine (T-DM1): mechanism of action of its cytotoxic component retained with improved tolerability. Toxicology and applied pharmacology, 2013, 273(2):298-313.
Poreba, "Protease-activated prodrugs: strategies, challenges, and future directions." The FEBS Journal, 2020, 287(10):1936-1969.
Pricop et al., "Differential modulation of stimulatory and inhibitory Fc gamma receptors on human monocytes by Th1 and Th2 cytokines", Journal of Immunology, 2001, 166(1):531-537.
Purdie and Benoiton, "Piperazinedione formation from esters of dipeptides containing glycine, alanine, and sarcosine: the kinetics in aqueous solution." Journal of the Chemical Society, Perkin Transactions 2, 1973, 14: 1845-1852.
Qi et al., "Serial determination of glomerular filtration rate in conscious mice using FITC-inulin clearance," American Journal of Physiology—Renal Physiology, Mar. 2004, 286(3):F590-F596.
Ramirez et al., "Defining causative factors contributing in the activation of hedgehog signaling in diffuse large B-cell lymphoma," Leuk Res., Oct. 2012, 36(10):1267-1273.
Randall et al., "Expression of murine CD38 defines a population of long-term reconstituting hematopoietic stem cells," Blood, May 15, 1996, 87(10):4057-4067.
Rataj et al., "High-affinity CD16-polymorphism and Fc-engineered antibodies enable activity of CD 16-chimeric antigen receptor-modified T cells for cancer therapy", British Journal of Cancer, 2019, 120(1):79-87.
Ravetch et al., "IgG Fc receptors", Annual Review of Immunology, 2001:19:275-290.
Reagan-Shaw et al., "Dose translation from animal to human studies revisited," FASEB J., Mar. 2008, 22(3):659-661.
Reinertsen et al., "B-Lymphocyte Alloantigens Associated with Systemic Lupus Erythematosus," The New England Journal of Medicine, Sep. 7, 1978, 299(10):515-518.
Remacle et al., "Membrane type I-matrix metalloproteinase (MT1-MMP) is internalised by two different pathways and is recycled to the cell surface." Journal of cell science, 2003, 116(19):3905-3916.
Remacle et al., "Novel MT1-MMP small-molecule inhibitors based on insights from hemopexin domain function in tumor growth," Cancer Res., May 1, 2012, 72(9):2339-2349.
Rhodes and Pei, "Bicyclic Peptides as Next-Generation Therapeutics," Chemistry, Sep. 18, 2017, 23(52):12690-12703.
Ridderstad and Tarlinton, "Kinetics of establishing the memory B cell population as revealed by CD38 expression," J Immunol., May 15, 1998, 160(10):4688-4695.
Riddle et al., "Tumor cell surface display of immunoglobulin heavy chain Fc by gene transfer as a means to mimic antibody therapy", Human Gene Therapy, 2005, 16(7):830-844.
Robert Gale, "Cancer treatment principles", Merck Manual consumer version (https://www.merckmanuals.com/home/cancer/prevention-and-treatment-of-cancer/cancer-treatment-principles?query=Cancer%20treatment Accessed May 8, 2020), Jul. 2018, 2 pages.
Robert Gale, "Overview of Cancer therapy", Merck Manual consumer version (https://www.merckmanuals.com/professional/hematology-and-oncology/principles-of-cancer-therapy/overview-of-cancer-therapy?query=Cancer Accessed May 8, 2020), Jul. 2018, 3 pages.
Robinson et al., "Integrative Clinical Genomics of Advanced Prostate Cancer", Cell, 2015, 161(5):1215-1228.
Rocca et al., "Phenotypic and Functional Dysregulated Blood NK Cells in Colorectal Cancer Patients Can Be Activated by Cetuximab Plus IL-2 or IL-15", Frontiers in Immunology, 2016, 7:413.
Rodan and Rodan, "Integrin function in osteoclasts," J Endocrinol., Sep. 1997, 154(Suppl):S47-S56.
Rodon et al., "Cantuzumab mertansine in a three-times a week schedule: a phase I and pharmacokinetic study." Cancer chemotherapy and pharmacology, 2008, 62(5):911-919.
Ross and Christiano, "Nothing but skin and bone," J Clin Invest., May 2006, 116(5):1140-1149.
Ross et al., "Bispecific T Cell Enager (BiTE) Antibody Constructs Can Mediate Bystander Tumor Cell Killing", PLoS ONE, Aug. 24, 2017, 12(8):1-24.
Rostovtsev et al., "A Stepwise Huisgen Cycloaddition Process: Copper(I)-Catalyzed Regioselective "Ligation" of Azides and Terminal Alkynes," Angewandte Chemie, Jul. 2002, 41(14):2596-2599.
Roth et al., "Docetaxel, cisplatin, and fluorouracil; docetaxel and cisplatin; and epirubicin, cisplatin, and fluorouracil as systemic treatment for advanced gastric carcinoma: a randomized phase II trial of the Swiss Group for Clinical Cancer Research", J Clin Oncol. Aug. 1, 2007, 25(22):3217-3023.
Rothwell et al., "Utility of ctDNA to support patient selection for early phase clinical trials: the TARGET study", Nature Medicine, 2019, 25(5):738-743.
Rudgers et al., "Binding properties of a peptide derived from beta-lactamase inhibitory protein." Antimicrob Agents Chemother., 2001, 45(12):3279-3286.
Salmon et al., "Human receptors for immunoglobulin G: key elements in the pathogenesis of rheumatic disease", Arthritis & Rheumatology, 2001, 44(4):739-750.
Satoh et al., "Experimental allergic encephalomyelitis mediated by murine encephalitogenic T cell lines specific for myelin proteolipid apoprotein," Journal of Immunology, Jan. 1987, 138(1):179-184.
Sausville and Burger, "Contributions of Human Tumor Xenografts to Anticancer Drug Development," Cancer Res., 2006, 66(7):3351-3354.
Scagliotti et al., "Phase III study comparing cisplatin plus gemcitabine with cisplatin plus pemetrexed in chemotherapy-naive patients with advanced-stage non-small-cell lung cancer." Journal of clinical oncology, 2008, 26(21):3543-3551.
Schiller et al., "Comparison of four chemotherapy regimens for advanced non-small-cell lung cancer." New England Journal of Medicine, 2002, 346(2):92-98.
Schreiber et al., "Rapid, electrostatically assisted association of proteins," Nature Structural & Molecular Biology, May 1996, 3:427-431.
Schulke et al., "The homodimer of prostate-specific membrane antigen is a functional target for cancer therapy," Proc Natl Acad Sci U SA., Oct. 28, 2003, 100(22):12590-12595.
Seely and Frazier, "Regulatory Forum Opinion Piece *: Dispelling Confusing Pathology Terminology: Recognition and Interpretation of Selected Rodent Renal Tubule Lesions," Toxicol Pathol., 2015, 43(4):457-463.
Segal et al., "Results from an Integrated Safety Analysis of Urelumab, an Agonist Anti-CD137 Monoclonal Antibody", clinical Cancer research, 2017, 23(8):1929-1936.
Seiki et al., "Membrane-type 1 matrix metalloproteinase: a key enzyme for tumor invasion." Cancer letters, 2003, 194(1):1-11.
Sepiashvili et al., "Potentially novel candidate biomarkers for head and neck squamous cell carcinoma identified using an integrated cell line-based discovery strategy." Molecular & Cellular Proteomics, 2012, 11(11):1404-1415.
Shaabani et al., "A patent review on PD-1/PD-L 1 antagonists: small molecules, peptides, and macrocycles (2015-2018)," Expert Opinion on Therapeutic Patents, 2018, 28(9):665-678.

(56) References Cited

OTHER PUBLICATIONS

Shah et al., "Phase I study of IMGN901, a CD56-targeting antibody-drug conjugate, in patients with CD56-positive solid tumors." Investigational new drugs, 2016, 34:290-299.
Shah, "Update on metastatic gastric and esophageal cancers." Journal of clinical oncology 33, No. 16 (2015): 1760-1769.
Shao et al., "Copy number variation is highly correlated with differential gene expression: a pan-cancer study," BMC Medical Genetics, Nov. 9, 2019, 20(1):175.
Shao et al., "CD137 ligand, a member of the tumor necrosis factor family, regulates immune responses via reverse signal transduction." Journal of leukocyte biology, 2011, 89(1):21-29.
Sharma et al., "Plasmacytoid dendritic cells from mouse tumor-draining lymph nodes directly activate mature Tregs via indoleamine 2, 3-dioxygenase", The Journal of clinical investigation, 2007, 117(9):2570-2582.
Shen et al., "Non-clinical disposition and metabolism of DM1, a Component of Trastuzumab Emtansine (T-DM1), in Sprague Dawley Rats." Drug Metabolism Letters, 2015, 9(2): 119-131.
Shi et al., "One-Bead-Two-Compound Thioether Bridged Macrocyclic (gamma)-AApeptide Screening Library Against EphA2," J Med Chem., Nov. 22, 2017, 60(22):9290-9298.
Shimauchi et al., "Augmented expression of programmed death-1 in both neoplastic and non-neoplastic CD4+ T-cells in adult T-cell leukemia/lymphoma", International journal of cancer, 2007, 121(12):2585-2590.
Sibaud et al., "Pigmentary disorders induced by anticancer agents. Part I: chemotherapy." In Annales de dermatologie et de venereologie, 2013, 140(3):183-196.
Siddharth et al., "Nectin-4 is a breast cancer stem cell marker that induces WNT/β-Catenin singaling via Pi3k/Akt axis," International Journal of Biochemistry and Cell Biology, 2017, 89:85-94.
Silver, "Multi-targeting by monotherapeutic antibacterials." Nat Rev Drug Discov., 2007, 6(1):41-55.
Smeenk et al., "Reconstructing the Discontinuous and Conformational β1/β3-Loop Binding Site on hFSH/hCG by Using Highly Constrained Multicyclic Peptides." ChemBioChem, 2015, 16(1):91-99.
Soderstrom, et al., "CD137: A checkpoint regulator involved in atherosclerosis." Atherosclerosis, 2018, 272:66-72.
Sordo-Bahamonde et al., "Mechanisms of Resistance to NK Cell Immunotherapy", Cancers (Basel). Apr. 7, 2020, 12(4):893.
Sounni et al."MT1-MMP expression promotes tumor growth and angiogenesis through an up-regulation of vascular endothelial growth factor expression" FASEB J., 2002, 16(6):555-564.
Sporn et at, "Chemoprevention of cancer." Carcinogenesis, 2000, 21(3):525-530.
Stathis et al., "A Phase I Study of IMGN529, an Antibody-Drug Conjugate (ADC) Targeting CD37, in Adult Patients with Relapsed or Refractory B-Cell Non-Hodgkin's Lymphoma (NHL)," Blood, 2014, 124(21):1760.
Steck et al., "Inside-out red cell membrane vesicles: preparation and purification," Science, Apr. 10, 1970, 168(3928):255-257.
Stein et al., "Eph receptors discriminate specific ligand oligomers to determine alternative signaling complexes, attachment, and assembly responses", Genes Development, 1998, 12(5):667-678.
Stevenson et al., "Preliminary studies for an immunotherapeutic approach to the C379ltreatment of human myeloma using chimeric anti-CD38 antibody," Blood, Mar. 1, 1991, 77(5):1071-1079.
Stojanovic et al., "Natural killer cells and solid tumors", Journal of Innate Immunity, 2011, 3(4):355-364.
Stringaris et al., "Leukemia-induced phenotypic and functional defects in natural killer cells predict failure to achieve remission in acute myeloid leukemia", Haematologica, May 2014, 99(5):836-847.
Strome et al., "B7-H1 blockade augments adoptive T-cell immunotherapy for squamous cell carcinoma", Cancer Res., 2003, 63(19):6501-6505.
Stuart et al., "Collagen Autoimmune Arthritis," Annual Review of Immunology, 1984, 2:199-218.
Sun et al., "Carbohydrate and protein immobilization onto solid surfaces by sequential Diels-Alder and azide-alkyne cycloadditions," Bioconjugate Chemistry, Jan.-Feb. 2006, 17(1):52-57.
Sun et al., "NK cell receptor imbalance and NK cell dysfunction in HBV infection and hepatocellular carcinoma", Cellular & Molecular Immunology, May 2015, 12(3):292-302.
Suojanen et aL., "A novel and selective membrane type-1 matrix metalloproteinase (MT1-MMP) inhibitor reduces cancer cell motility and tumor growth," Cancer Biology & Therapy, Dec. 2009, 8(24):2362-2370.
Supuran, "Carbonic anhydrases: novel therapeutic applications for inhibitors and activators," Nature Reviews Drug Discovery, Feb. 2008, 7(2):168-181.
Tandon et al., "Emerging strategies for EphA2 receptor targeting for cancer therapeutics" Expert Opinion on Therapeutic Targets, 2011, 15(1):31-51.
Tarazona et al., "Current progress in NK cell biology and NK cell-based cancer immunotherapy", Cancer Immunol Immunother, 2020, 69(5):879-899.
Tasch et al., "A unique folate hydrolase, prostate-specific membrane antigen (PSMA): a target for immunotherapy?", Crit Rev Immunol., 2001, 21(1-3):249-261.
Teitelbaum, "Osteoclasts, integrins, and osteoporosis," J Bone Miner Metab., Oct. 2000, 18(6):344-349.
Teitelbaum, "Osteoporosis and Integrins," The Journal of Clinical Endocrinology & Metabolism, Apr. 2005, 90(4):2466-2468.
Teti et al., "The Role of the AlphaVbeta3 Integrin in the Development of Osteolytic Bone Metastases: A Pharmacological Target for Alternative Therapy?", Calcified Tissue International, Oct. 2002, 71(4):293-299.
Tetu et al., "The influence of MMP-14, TIMP-2 and MMP-2 expression on breast cancer prognosis." Breast Cancer Research, 2006, 8(3):1-9.
Teufel et al., "Backbone-driven collapse in unfolded protein chains," J Mol Biol., Jun. 3, 2011, 409(2):250-262.
Thake et al., "Toxicity of Maytansine (NSC 153858) in dogs and monkeys." PB-US National Technical Information Service (1975), Feb. 1975, 244628.
Thevenard et al., "The YSNSG cyclopeptide derived from tumstatin inhibits tumor angiogenesis by down-regulating endothelial cell migration." International journal of cancer, 2010, 126(5):1055-1066.
Thompson et al., "Costimulatory B7-H1 in renal cell carcinoma patients: Indicator of tumor aggressiveness and potential therapeutic target", Proceedings of the National Academy of Sciences, 2004, 101(49):17174-17179.
Timmerman et al., "Rapid and Quantitative Cyclization of Multiple Peptide Loops onto Synthetic Scaffolds for Structural Mimicry of Protein Surfaces," ChemBioChem, 2005, 6(5):821-824.
Todisco et al., "CD38 ligation inhibits normal and leukemic myelopoiesis," Blood, Jan. 2000, 95(2):535-542.
Tolcher et al., "Cantuzumab mertansine, a maytansinoid immunoconjugate directed to the CanAg antigen: a phase I, pharmacokinetic, and biologic correlative study." Journal of clinical oncology, 2003, 21(2):211-222.
Toogood, "Small Molecule Immuno-oncology Therapeutic Agents," Bioorganic & Medicinal Chemistry Letters, 2018, 28(3):319-329.
Touati et al., "Phage Selection of Bicyclic Peptide Ligands and Development of a New Peptide Cyclisation Method", Theses No. 5536, Oct. 2012, 117 pages.
Trouche et al., "Small multivalent architectures mimicking homotrimers of the TNF superfamily member CD40L: delineating the relationship between structure and effector function." Journal of the American Chemical Society, 2007, 129(44):13480-13492.
Trudel et al., "Membrane-type-1 matrix metalloproteinase, matrix metalloproteinase 2, and tissue inhibitor of matrix proteinase 2 in prostate cancer: identification of patients with poor prognosis by immunohistochemistry." Human pathology, 2008, 39(5):731-739.
Tugyi et al., "Partial D-amino acid substitution: Improved enzymatic stability and preserved Ab recognition of a MUC2 epitope peptide," Proceedings of the National Academy of Sciences U.S.A., Jan. 2005, 102(2):413-418.

(56) References Cited

OTHER PUBLICATIONS

Tutt et al., "Abstract S3-01: the TNT trial: a randomized phase III trial of carboplatin (C) compared with docetaxel (D) for patients with metastatic or recurrent locally advanced triple negative or BRCA1/2 breast cancer (CRUK/07/012)." Cancer Research, May 2015, 75(9_Suppl):S3-01.
Uckun, "Regulation of human B-cell ontogeny," Blood, Nov. 1990, 76(10): 1908-1923.
Ulasov et al., "Inhibition of MMP 14 potentiates the therapeutic effect of temozolomide and radiation in gliomas." Cancer medicine, 2013, 2(4):457-467.
Ün, Sanya. Charakterisierung von Peptiden für die Bindung essentieller Penicillin-bindender Proteine und die Variationen der Linkerlänge einzelkettiger TetR Varianten. Friedrich-Alexander-Universitaet Erlangen-Nuernberg (Germany), 2010. 139 pages.
Upadhyaya, "Activation of CD137 using multivalent and tumor targeted Bicyclic peptides." Cancer Research, Jul. 2019, 79(13 Suppl):3257-3257.
Van Eden et al., "Cloning of the mycobacterial epitope recognized by T lymphocytes in adjuvant arthritis," Nature, Jan. 14, 1988, 331(6152):171-173.
Van Glabbeke et al., "Progression-free rate as the principal endpoint for phase II trials in soft-tissue sarcomas." European Journal of Cancer, 2002, 38(4):543-549.
Vandenbroucke and Libert, "Is there new hope for therapeutic matrix metalloproteinase inhibition ?. " Nature reviews Drug discovery, 2014, 13(12):904-927.
Walker-Daniels et al., "Overexpression of the EphA2 tyrosine kinase in prostate cancer", Prostate, 1999, 41(4):275-280.
Wallbrecher et al., "Exploration of the design principles of a cell-penetrating bicylic peptide scaffold," Bioconjug Chem., May 21, 2014, 25(5):955-964.
Wang et al., "Co-expression of MMP-14 and MMP-19 predicts poor survival in human glioma." Clinical and Translational Oncology, 2013, 15:139-145.
Wang et al., "MMP-14 overexpression correlates with poor prognosis in non-small cell lung cancer." Tumor Biology, 2014, 35:9815-9821.
Wang et al., "Probing for Integrin αvβ3 Binding of RGD Peptides Using Fluorescence Polarization," Bioconjugate Chem., May-Jun. 2005, 16(3):729-734.
Wang, "An exact mathematical expression for describing competitive binding of two different ligands to a protein molecule." FEBS letters, 1995, 360(2):111-114.
Watanabe et al., "NK cell dysfunction with down-regulated CD16 and up-regulated CD56 molecules in patients with esophageal squamous cell carcinoma", Diseases of the Esophagus, 2010, 23(8):675-681.
Waterhouse et al., "Safety profile of nivolumab administered as 30-min infusion: analysis of data from CheckMate 153," Cancer Chemother Pharmacol., Apr. 2018, 81(4):679-686.
Watts, "TNF/TNFR family members in costimulation of T cell responses", Annu. Rev, Immunol., Apr. 2005, 23:23-68.
Weber, J. "Immune Checkpoint Proteins: A New Therapeutic Paradigm for Cancer—Preclinical Background: CTLA-4 and PD-1 Blockade", Seminars in Oncology, Oct. 2010, 37(5):430-439.
Wei et al., "Discovery of Peptidomimetic Antibody—Drug Conjugate Linkers with Enhanced Protease Specificity," J. Med. Chem., 2018, 61(3):989-1000.
Wind et al., "Measuring carbonic anhydrase IX as a hypoxia biomarker: differences in concentrations in serum and plasma using a commercial enzyme-linked immunosorbent assay due to influ¬ences of metal ions," Annals of Clinical Biochemistry, Mar. 2011, 48(2):112-120.
Winter et al., "Making antibodies by phage display technology," Annual Review of Immunology, 1994, 12:433-455.
Wu et al., "Structures of the CXCR4 chemokine GPCR with small-molecule and cyclic peptide antagonists," Science, Nov. 2010, 330(6007):1066-1071.
Wu et al., "A novel polymorphism of FcgammaRIIIa (CD16) alters receptor function and predisposes to autoimmune disease", The Journal of Clinical Investigation, 1997, 100(5):1059-1070.
Wu et al., "Design and Characterization of Novel EphA2 Agonists for Targeted Delivery of Chemotherapy to Cancer Cells," Chem. Biol., 2015, 22(7):876-887.
Wu et al., "Natural killer cells in cancer biology and therapy", Molecular Cancer, Aug. 6, 2020, 19(1):120, 26 pages.
Wu et al., "Immunohistochemical localization of programmed death-1 ligand-1 (PD-L1) in gastric carcinoma and its clinical significance" Acta histochemica, 2006, 108(1):19-24.
Wykosky et al., "EphA2 as a novel molecular marker and target in glioblastoma multiforme", Molecular Cancer Research, Oct. 2005, 3(10):541-551.
Xiong et al., "Crystal structure of the extracellular segment of integrin aVB3 in complex with an Arg-Gly-Asp Ligand", Science, Apr. 2002, 296(5565):151-155.
Yang et al., "Overexpression of EphA2, MMP-9, and MVD-CD34 in hepatocellular carcinoma: Implications for tumor progression and prognosis," Hepatol Res., 2009, 39(12):1169-1177.
Yardley et al., "Emerge: a randomized phase II study of the antibody-drug conjugate glembatumumab vedotin in advanced glycoprotein NMB-expressing breast cancer." Journal of clinical oncology: official journal of the American Society of Clinical Oncology, 2015, 33(14):1609.
Yoon et al., "An efficient strategy for cell-based antibody library selection using an integrated vector system," BMC Biotechnology, 2012, 12(62):10 pages.
Yoshihara et al., "Tags for labeling protein N-termini with subtiligase for proteomics," Bioorganic & Medicinal Chemistry Letters, Nov. 2008, 18(22):6000-6003.
Yu and Taylor, "A new strategy applied to the synthesis of an a-helical bicyclic peptide constrained by two overlapping i, i+ 7 side-chain bridges of novel design." Tetrahedron letters, 1996, 37(11):1731-1734.
Yuan et al., "Neuropilin-1 and the development progress of the same as a therapeutic target for malignant tumors," Tumor, 2016, 36:358-364.
Yuan et al., "Over-expression of EphA2 and EphrinA-1 in human gastric adenocarcinoma and its prognostic value for postoperative patients," Dig Dis Sci., Nov. 2009, 54(11):2410-2417.
Zarrabi et al., "Inhibition of matrix metalloproteinase 14 (MMP-14)-mediated cancer cell migration." Journal of Biological Chemistry, 2011, 286(38):33167-33177.
Zelinski et al., "EphA2 Overexpression Causes Tumorigenesis of Mammary Epithelial Cells," Cancer research, Mar. 2001, 61(5):2301-2306.
Zervosen et al., "Development of New Drugs for an Old Target-The Penicillin Binding Proteins." Molecules. 2012:17 (11);12478-12505.
Zhang et al., "A new anti-HER2 antibody that enhances the antitumor efficacy of trastuzumab and pertuzumab with a distinct mechanism of action", Mol Immunol., 2020, 119:48-58.
Zhang et al., "FCGR2A and FCGR3A Polymorphisms Associated With Clinical Outcome of Epidermal Growth Factor Receptor-Expressing Metastatic Colorectal Cancer Patients Treated With Single-Agent Cetuximab", Journal of Clinical Oncology, 2007, 25(24):3712-3718.
Zhao el al., "Structural basis of specificity of a peptidyl urokinase inhibitor, upain-1," Journal of Structural Biology, Oct. 2007, 160(1):1-10.
Zhou et al., "Significance of semaphorin-3A and MMP-14 protein expression in non-small cell lung cancer", Oncology letters, 2014, 7(5):1395-1400.
Zhu et al., "High-affinity peptide against MT1-MMP for in vivo tumor imaging." Journal of controlled release, 2011, 150(3):248-255.
Zhuang et al., "Elevation of receptor tyrosine kinase EphA2 mediates resistance to trastuzumab therapy," Cancer Res., Jan. 1, 2010, 70(1):299-308.
Zilber et al., "CD38 expressed on human monocytes: a coaccessory molecule in the superantigeninduced proliferation," Proc Natl Acad Sci US A., Mar. 14, 2000, 97(6):2840-2845.

(56) References Cited

OTHER PUBLICATIONS

Zou et al., "PD-L1 (B7-H1) and PD-1 Pathway Blockade for Cancer Therapy: Mechanisms, Response Biomarkers and Combinations," Sci. Transl. Med., 2016, 8(328):328rv4., 1-14.
Zubiaur et al., "CD38 Ligation Results in Activation of the Raf-1/Mitogen-Activated Protein Kinase and the CD3-zeta/zeta-Associated Protein-70 Signaling Pathways in Jurkat T Lymphocytes," J Immunol., Jul. 1, 1997, 159(1):193-205.
Zugazagoitia et al., "Current Challenges in Cancer Treatment," Clinical Therapies, 2016, 38(7):1551-1566.
Zupo et al., "CD38 signaling by agonistic monoclonal antibody prevents apoptosis of human germinal center B cells," Eur J Immunol., May 1994, 24(5):1218-1222.
PCT International Preliminary Report on Patentability received for PCT/GB2019/053536, dated Jun. 24, 2021, 07 pages.
PCT International Preliminary Report on Patentability received for PCT/EP2017/083953, dated Jul. 4, 2019, 7 pages.
PCT International Preliminary Report on Patentability received for PCT/EP2017/083954, dated Jul. 4, 2019, 7 pages.
PCT International Preliminary Report on Patentability received for PCT/EP2019/066010, dated Dec. 30, 2020, 9 pages.
PCT International Preliminary Report on Patentability received for PCT/EP2019/066066, dated Dec. 30, 2020, 8 pages.
PCT International Preliminary Report on Patentability received for PCT/EP2019/066273, dated Dec. 30, 2020, 8 pages.
PCT International Preliminary Report on Patentability received for PCT/EP2021/072866, dated Mar. 2, 2023, 13 pages.
PCT International Preliminary Report on Patentability received for PCT/GB2015/053247, dated May 11, 2017, 8 pages.
PCT International Preliminary Report on Patentability received for PCT/GB2018/050017, dated Jul. 18, 2019, 8 pages.
PCT International Preliminary Report on Patentability received for PCT/GB2018/052222, dated Feb. 13, 2020, 7 pages.
PCT International Preliminary Report on Patentability received for PCT/GB2019/050485, dated Sep. 3, 2020, 8 pages.
PCT International Preliminary Report on Patentability received for PCT/GB2019/053537, dated Jun. 24, 2021, 7 pages.
PCT International Preliminary Report on Patentability received for PCT/GB2019/053679, dated Jul. 1, 2021, 7 pages.
PCT International Preliminary Report on Patentability received for PCT/GB2019/053680, dated Jul. 1, 2021, 7 pages.
PCT International Preliminary Report on Patentability received for PCT/GB2020/050069, dated Jul. 29, 2021, 8 pages.
PCT International Preliminary Report on Patentability received for PCT/GB2020/050070, dated Jul. 29, 2021, 11 pages.
PCT International Preliminary Report on Patentability received for PCT/GB2020/050071, dated Jul. 29, 2021, 7 pages.
PCT International Preliminary Report on Patentability received for PCT/GB2020/050072, dated Jul. 29, 2021, 11 pages.
PCT International Preliminary Report on Patentability received for PCT/GB2020/050073, dated Jul. 29, 2021, 8 pages.
PCT International Preliminary Report on Patentability received for PCT/GB2020/050074, dated Jul. 29, 2021, 14 pages.
PCT International Preliminary Report on Patentability received for PCT/GB2020/052058, dated Mar. 10, 2022, 8 pages.
PCT International Preliminary Report on Patentability received for PCT/GB2020/052590, dated Apr. 28, 2022, 7 pages.
PCT International Preliminary Report on Patentability received for PCT/GB2021/050490, dated Sep. 9, 2022, 9 pages.
PCT International Preliminary Report on Patentability received for PCT/GB2021/050491, dated Sep. 9, 2022, 10 pages.
PCT International Preliminary Report on Patentability received for PCT/GB2022/050043, dated Jul. 20, 2023, 13 pages.
PCT International Preliminary Report on Patentability received for PCT/EP2018/060498, dated Nov. 7, 2019. 8 Pages.
PCT International Preliminary Report on Patentability received for PCT/EP2019/065993, dated Dec. 30, 2020, 7 pages.
PCT International Preliminary Report on Patentability received for PCT/GB2017/053560, dated Jun. 6, 2019, 7 pages.
PCT International Preliminary Report on Patentability received for PCT/GB2018/051779, dated Jan. 9, 2020, 6 pages.
PCT International Preliminary Report on Patentability received for PCT/GB2018/053676, dated Jul. 2, 2020, 7 pages.
PCT International Preliminary Report on Patentability received for PCT/GB2018/053678, dated Jul. 2, 2020, 9 pages.
PCT International Preliminary Report on Patentability received for PCT/GB2019/051740, dated Dec. 30, 2020, 8 pages.
PCT International Preliminary Report on Patentability received for PCT/GB2019/051741, dated Dec. 30, 2020, 7 pages.
PCT International Preliminary Report on Patentability received for PCT/GB2019/053020, dated May 6, 2021, 12 pages.
PCT International Preliminary Report on Patentability received for PCT/GB2019/053080, dated May 14, 2021, 16 pages.
PCT International Preliminary Report on Patentability received for PCT/GB2019/053539, dated Jun. 24, 2021, 7 pages.
PCT International Preliminary Report on Patentability received for PCT/GB2019/053540, dated Jun. 24, 2021, 8 pages.
PCT International Preliminary Report on Patentability received for PCT/GB2020/050505, dated Sep. 16, 2021, 7 pages.
PCT International Preliminary Report on Patentability received for PCT/GB2020/050874, dated Oct. 14, 2021, 11 pages.
PCT International Preliminary Report on Patentability received for PCT/GB2020/051140, dated Nov. 25, 2021, 8 pages.
PCT International Preliminary Report on Patentability received for PCT/GB2020/051144, dated Nov. 18, 2021, 9 pages.
PCT International Preliminary Report on Patentability received for PCT/GB2020/051827, dated Feb. 10, 2022, 8 pages.
PCT International Preliminary Report on Patentability received for PCT/GB2020/051829, dated Feb. 10, 2022 , 8 pages.
PCT International Preliminary Report on Patentability received for PCT/GB2020/051831, dated Feb. 10, 2022, 10 pages.
PCT International Preliminary Report on Patentability received for PCT/GB2020/051923, dated Feb. 24, 2022, 9 pages.
PCT International Preliminary Report on Patentability received for PCT/GB2020/052445, dated Apr. 14, 2022, 26 pages.
PCT International Preliminary Report on Patentability received for PCT/GB2020/052619, dated Apr. 28, 2022, 9 pages.
PCT International Preliminary Report on Patentability received for PCT/GB2020/053026, dated Jun. 9, 2022, 8 pages.
PCT International Preliminary Report on Patentability received for PCT/GB2021/051220, dated Dec. 1, 2022, 7 pages.
PCT International Preliminary Report on Patentability received for PCT/GB2021/051451, dated Dec. 22, 2022, 09 pages.
PCT International Preliminary Report on Patentability received for PCT/GB2021/052001, dated Feb. 16, 2023, 13 pages.
PCT International Preliminary Report on Patentability received for PCT/GB2022/050044, dated Jul. 20, 2023, 13 pages.
PCT International Preliminary Report on Patentability received for PCT/GB2022/050055, dated Jul. 20, 2023, 17 pages.
PCT International Preliminary Report on Patentability received for PCT/GB2017/051250, dated Nov. 15, 2018, 7 pages.
PCT International Preliminary Report on Patentability received for PCT/GB2018/051118, dated Nov. 7, 2019, 11 pages.
PCT International Search Report and Written Opinion received for PCT/EP2017/083953, dated May 9, 2018, 9 pages.
PCT International Search Report and Written Opinion received for PCT/EP2017/083954, dated May 4, 2018, 9 pages.
PCT International Search Report and Written Opinion received for PCT/EP2018/060498, dated Jul. 5, 2018, 13 pages.
PCT International Search Report and Written Opinion received for PCT/EP2019/065993, dated Sep. 24, 2019, 11 pages.
PCT International Search Report and Written Opinion received for PCT/EP2019/066010, dated Sep. 30, 2019, 12 pages.
PCT International Search Report and Written Opinion received for PCT/EP2019/066066, dated Oct. 1, 2019, 11 pages.
PCT International Search Report and Written Opinion received for PCT/EP2021/072866, dated Dec. 21, 2021, 21 pages.
PCT International Search Report and Written Opinion received for PCT/GB2015/053247, dated Jan. 27, 2016, 12 pages.
PCT International Search Report and Written Opinion received for PCT/GB2017/051250, dated Aug. 4, 2017, 10 pages.

(56) References Cited

OTHER PUBLICATIONS

PCT International Search Report and Written Opinion received for PCT/GB2017/053560, dated Jul. 2, 2018, 9 pages.
PCT International Search Report and Written Opinion received for PCT/GB2018/050017, dated Mar. 23, 2018, 12 pages.
PCT International Search Report and Written Opinion received for PCT/GB2018/051118, dated Aug. 3, 2018, 20 pages.
PCT International Search Report and Written Opinion received for PCT/GB2018/051779, dated Sep. 3, 2018, 10 pages.
PCT International Search Report and Written Opinion received for PCT/GB2018/053676, dated Mar. 21, 2019, 12 pages.
PCT International Search Report and Written Opinion received for PCT/GB2018/053678, dated Mar. 20, 2019, 12 pages.
PCT International Search Report and Written Opinion received for PCT/GB2019/050485, dated Jun. 4, 2019, 12 Pages.
PCT International Search Report and Written Opinion received for PCT/GB2019/050951, dated Jul. 4, 2019, 11 pages.
PCT International Search Report and Written Opinion received for PCT/GB2019/051740, dated Aug. 29, 2019, 11 pages.
PCT International Search Report and Written Opinion received for PCT/GB2019/051741, dated Aug. 5, 2019, 10 pages.
PCT International Search Report and Written Opinion received for PCT/GB2019/053020, dated Jun. 23, 2020, 19 pages.
PCT International Search Report and Written Opinion received for PCT/GB2019/053080, dated Feb. 7, 2020, 19 pages.
PCT International Search Report and Written Opinion received for PCT/GB2019/053537, dated Mar. 11, 2020, 10 pages.
PCT International Search Report and Written Opinion received for PCT/GB2019/053539, dated Mar. 11, 2020, 8 pages.
PCT International Search Report and Written Opinion received for PCT/GB2019/053540, dated Mar. 11, 2020, 10 pages.
PCT International Search Report and Written Opinion received for PCT/GB2019/053679, dated Mar. 11, 2020, 12 pages.
PCT International Search Report and Written Opinion received for PCT/GB2019/053680, dated Mar. 11, 2020, 11 pages.
PCT International Search Report and Written Opinion received for PCT/GB2020/050069, dated Apr. 15, 2020, 10 pages.
PCT International Search Report and Written Opinion received for PCT/GB2020/050070, dated Jun. 23, 2020, 16 pages.
PCT International Search Report and Written Opinion received for PCT/GB2020/050071, dated May 12, 2020, 10 pages.
PCT International Search Report and Written Opinion received for PCT/GB2020/050072, dated Jun. 30, 2020, 16 pages.
PCT International Search Report and Written Opinion received for PCT/GB2020/050073, dated Apr. 7, 2020, 11 pages.
PCT International Search Report and Written Opinion received for PCT/GB2020/050074, dated Jun. 23, 2020, 21 pages.
PCT International Search Report and Written Opinion received for PCT/GB2020/050505, dated Apr. 28, 2020, 9 pages.
PCT International Search Report and Written Opinion received for PCT/GB2020/050874, dated Jun. 17, 2020, 15 pages.
PCT International Search Report and Written Opinion received for PCT/GB2020/051140, dated Aug. 20, 2020, 10 pages.
PCT International Search Report and Written Opinion received for PCT/GB2020/051144, dated Aug. 18, 2020, 12 pages.
PCT International Search Report and Written Opinion received for PCT/GB2020/051827, dated Nov. 3, 2020, 11 pages.
PCT International Search Report and Written Opinion received for PCT/GB2020/051829, dated Oct. 30, 2020, 11 pages.
PCT International Search Report and Written Opinion received for PCT/GB2020/051831, dated Nov. 4, 2020, 13 pages.
PCT International Search Report and Written Opinion received for PCT/GB2020/051923, dated Nov. 17, 2020, 12 pages.
PCT International Search Report and Written Opinion received for PCT/GB2020/052058, dated Nov. 12, 2020, 11 pages.
PCT International Search Report and Written Opinion received for PCT/GB2020/052445, dated Mar. 4, 2021, 34 pages.
PCT International Search Report and Written Opinion received for PCT/GB2020/052590, dated Jan. 28, 2021, 9 pages.
PCT International Search Report and Written Opinion received for PCT/GB2020/052619, dated Jan. 28, 2021, 12 pages.
PCT International Search Report and Written Opinion received for PCT/GB2020/053026, dated Mar. 23, 2021, 11 pages.
PCT International Search Report and Written Opinion received for PCT/GB2021/050490, dated May 19, 2021, 12 pages.
PCT International Search Report and Written Opinion received for PCT/GB2021/050491, dated May 14, 2021, 14 pages.
PCT International Search Report and Written Opinion received for PCT/GB2021/051220, dated Aug. 27, 2021, 12 pages.
PCT International Search Report and Written Opinion received for PCT/GB2021/051451, dated Sep. 22, 2021, 14 pages.
PCT International Search Report and Written Opinion received for PCT/GB2021/052001, dated Nov. 12, 2021, 11 pages.
PCT International Search Report and Written Opinion received for PCT/GB2022/050043, dated Nov. 17, 2022, 18 pages.
PCT International Search Report and Written Opinion received for PCT/GB2022/050044, dated Jun. 28, 2022, 19 pages.
PCT International Search Report and Written Opinion received for PCT/GB2022/050055, dated Apr. 19, 2022, 21 pages.
PCT International Search Report and Written Opinion received for PCT/GB2022/052249, dated Mar. 28, 2023, 14 pages.
PCT International Search Report and Written Opinion received for PCT/GB2022/052903, dated Mar. 13, 2023, 12 pages.
PCT International Search Report and Written Opinionreceived for PCT/GB2018/052222, dated Oct. 11, 2018, 9 pages.
U.S. Appl. No. 17/769,668, filed Apr. 15, 2022.
U.S. Appl. No. 18/021,748, filed Feb. 16, 2023.
U.S. Appl. No. 18/271,360, filed Jul. 7, 2023.
U.S. Appl. No. 18/271,593, filed Jul. 10, 2023.
U.S. Appl. No. 18/313,983, filed May 8, 2023.
U.S. Appl. No. 18/345,506, filed Jun. 30, 2023.
Chen et al., "Peptide ligands stabilized by small molecules," Angew Chem Int Ed Engl. 2014;53(6):1602-6.
Deonarain et al., "Small-Format Drug Conjugates: A Viable Alternative to ADCs for Solid Tumours?" Antibodies (Basel). 2018;7(2):16.
Heinis et al., "Phage-encoded combinatorial chemical libraries based on bicyclic peptides," Nat Chem Biol. 2009;5 (7):502-7.
PCT Search Report and Written Opinion issued in PCT/EP2019/066273, dated Sep. 20, 2019.
PCT Search Report and Written Opinion issued in PCT/GB2019/053536, dated Mar. 2, 2020.
Shen et al., "Evaluation of Phage Display Discovered Peptides as Ligands for Prostate-Specific Membrane Antigen (Psma)," PLoS One. 2013;8(7):e68339.
"Bicycle Therapeutics Investor Presentation", Retrieved from: https://investors.bicycletherapeutics.com/static-files/f456c054-95c8-4e19-a62a-fcf5feb0650b, Aug. 2024, 61 pages.
Adley et al., "Expression of membrane type 1 matrix metalloproteinase (MMP-14) in epithelial ovarian cancer: High level expression in clear cell carcinoma", Gynecologic Oncology, 2009, 112(2):319-324.
Anonymous, "Bicycle Therapeutics 2023 R&D Day Deck", Retrieved from: https://investors.bicycletherapeutics.com/static-files/46599fde-67dc-40a8-9dcb-10ed8444f3le, Dec. 14, 2023, 155 pages.
Anonymous, "Bicycle Therapeutics BT8009 Regulatory Update", Retrieved from: https://investors.bicycletherapeutics.com/static-files/265210c3-233f-4dd8-af32-d34592398d85, Sep. 11, 2023, 23 pages.
Anonymous, "UPI000011DEEB", Retrieved from: https://www.uniprot.org/uniparc/UPI000011DEEB, 2014, 2 pages.
Bader et al., "Abstract 3088: Breaking from the paradigm of antibody-drug conjugates: Evaluation of clinical pharmacokinetics and safety of Bicycle Toxin Conjugates® (BTCs)", American Society of Clinical Oncology Annual Meeting, May 31-Jun. 4, 2024, pp. 1-9.
Baldini et al., "Abstract 498: BT8009-100: A Phase I/II Study of Novel Bicyclic Peptide and MMAE Conjugate BT8009 in Patients (pts) with Advanced Malignancies Associated with Nectin-4 Expression, Including Urothelial Cancer (UC)", ASCO Genitourinary (GU) Cancers Symposium Conference, Feb. 17, 2023, pp. 1-6.
Banerji et al., "A Cancer Research UK phase I/IIa trial of BT1718 (a first in class Bicycle Toxin Conjugate) given intravenously in patients with advanced solid tumours", ASCO, Jun. 5, 2018, pp. 1-4.

(56) References Cited

OTHER PUBLICATIONS

Banerji et al., "A Cancer Research UK phase I/IIa trial of BT1718 (a first in class Bicycle Toxin Conjugate) given intravenously in patients with advanced solid tumours", NCRI, Oct. 1, 2018, 1 page.
Battula et al., "Abstract 4613: A novel fully synthetic dual targeted EphA2/CD137 Bicycle® peptide induces tumor localized CD137 agonism", American Association of Cancer Research, Jun. 22, 2020, pp. 1-4.
Battula et al., "Abstract P794: A novel fully synthetic dual targeted EphA2/4-1BB Bicycle® peptide induces tumor localized 4-1BB agonism", SITC, Nov. 9, 2019, pp. 1-4.
Bendell et al., "TPS3655: BT5528-100 Phase I/II Study; Safety, Pharmacokinetics & Preliminary Clinical Activity of BT5528 in Patients with Advanced Malignancies Associated with EphA2 Expression", ASCO, May 29, 2020, 1 page.
Bennett et al., "Abstract 1167/2: Development of BT1718, a novel Bicycle Drug Conjugate for the treatment of lung cancer", American Association of Cancer Research, Apr. 1, 2017, pp. 1-4.
Bennett et al., "Abstract 164: BT5528, an EphA2-targeting Bicycle Toxin Conjugate (BTC): profound efficacy without bleeding and coagulation abnormalities in animal models", EORTC, Nov. 13, 2018, pp. 1-6.
Bennett et al., "Abstract 5854: BT5528, a Bicycle Toxin Conjugate (BTC) targeting EphA2 has potent antitumour activity without bleeding or coagulation abnormalities in animal models", American Association of Cancer Research, Apr. 14, 2018, pp. 1-6.
Bennett et al., "Abstract 5855: Bicycle Toxin Conjugates (BTCs) targeting EphA2 for the treatment of solid tumours: Discovery and selection of BT5528", American Association of Cancer Research, Apr. 14, 2018, pp. 1-8.
Bennett et al., "Abstract C066: BT5528, a Bicycle Toxin Conjugate targeting EphA2: mechanism of action and clinical translation", AACR-NCI-EORTC, Oct. 29, 2019, pp. 1-6.
Bennett, "Abstract 4481: BT5528, an EphA2-targeting Bicycle® Toxin Conjugate (BTC): Profound efficacy without bleeding and coagulation abnormalities in animal models", AACR Annual Meeting, Apr. 4, 2019, 11 pages.
Bennett, "Bicycle Conjugates to Target Solid Tumors", Next Generation Conjugates Summit, Feb. 27, 2023, 23 pages.
Bennett, "BT5528: A Bicycle Toxin Conjugate Targeting EphA2 for the Treatment of Solid Tumours", 9th Annual World ADC Conference, Mar. 6, 2019, 13 pages.
Bournakas et al., "PBP inhibitors discovered using a modified phage display platform (Bicycles)", ESCMID, Oct. 11, 2022, 1 page.
Brandish, "Bicycle Therapeutics: Precision-guided immune agonism for the treatment of cancer", Immuno UK meeting, Sep. 30, 2022, 25 pages.
Campbell et al., "Poster 1197: A multi tumor survey of Nectin-4 expression to guide BT8009 indication selection", American Association of Cancer Research, Apr. 12, 2021, pp. 1-4.
Campbell et al., "Poster 5300: A survey of EphA2 expression by immunohistochemistry (IHC) in tumor tissue microarrays (TMAs) to support BT5528 indication selection", American Association of Cancer Research, Jun. 22, 2020, pp. 1-6.
Carabateas et al., "Strong Analgesics, Some 1-Substituted 4-Phenyl-4-Propionoxypiperidines", Journal of Medicinal and Pharmaceutical Chemistry, Sep. 1962, 5:913-919.
CAS No. 18226-42-1, "1,3,5-Tris(bromomethyl)benzene", Chemical Book, Retrieved from: https://www.chemicalbook.com/ProductChemicalPropertiesCB0500171_EN.htm, 2023, 2 pages.
Center for Pancreatic and Biliary Diseases, "Bile Duct Cancer", University of Southern California, Department of Surgery, Dec. 7, 2017, Retrieved from: https://web.archive.org/web/20171207023733/http://www.surgery.usc.edu:80/divisions/tumor/PancreasDiseases/web%20pages/BILIARY%20SYSTEM/cholangiocarcinoma.html, 3 pages.
Chen et al., "Abstract A8: Novel Multimers of Bicyclic Peptides Cluster and Activate CD137 (4-1BB): A Costimulatory T-Cell Checkpoint Receptor", PEGS, Nov. 12, 2018, pp. 1-7.
Cohen et al., "Abstract 2: Quantitation of CD137 and Nectin-4 expression across multiple tumor types to support indication selection for BT7480, a Bicycle tumor-targeted immune cell agonistTM (Bicycle TICA™)", SITC, Nov. 12, 2021, pp. 1-7.
Cohen et al., "Abstract 5555: Development of a CD137 receptor occupancy assay to support the phase I/II study of BT7480, a Bicycle® tumor-targeted immune cell agonist (Bicycle TICA™)", American Association of Cancer Research, Apr. 8, 2022, pp. 1-6.
Cohen et al., "Abstract A65: Development of a CD137 receptor occupancy assay to support the phase I/II study of BT7480, a Bicycle tumor-targeted immune cell agonist® (Bicycle TICA™)", AACR-BC-EORTC, Oct. 26, 2022, pp. 1-7.
Cohen, "Translating preclinical findings into clinical biomarker assays to support the Phase I/II study of BT7480, a Bicycle tumor-targeted immune cell agonist®", World Clinical Biomarkers & CDx Summit, Sep. 28, 2022, 21 pages.
Cohen, "Turning preclinical findings into clinic-ready biomarker assays to support BT7480 development", Markets and Markets Biomarker and Companion Diagnostics Conference, Feb. 15, 2023, 21 pages.
Cook et al., "Abstract 5764: Pharmacokinetic (PK) assessment of BT1718: A phase 1/2a study of BT1718, a first in class bicycle toxin conjugate (BTC), in patients with advanced solid tumours", EMSO, Sep. 28, 2019, pp. 1-4.
Cooke, "Bicycles as precision guided therapeutics", UK Symposium: Advancing Drug Discovery for Oncology, Mar. 13, 2023, 15 pages.
Drumm et al., "Genetic Variation and Clinical Heterogeneity in Cystic Fibrosis", Annu. Rev. Pathol. Mech. Dis., 2012, 7:267-282.
Dufort et al., "Abstract 1340: Modulation of the natural killer cell immune response to tumor with a synthetic tumor-immune cell agonist, NK-TICA®", American Association for Cancer Research Annual Meeting, Apr. 8, 2024, pp. 1-6.
Dufort et al., "Abstract 15699: Generation of a Bicycle NK-TICA™, a novel NK cell engaging molecule designed to induce targeted tumor cytotoxicity", SITC, Nov. 12, 2022, pp. 1-5.
Dufort et al., Abstract 1806: Modulation of the natural killer (NK) cell immune response to tumor with novel synthetic tumor-immune cell agonist, NK-TICA™, American Association for Cancer Research Annual Meeting, Apr. 17, 2023, pp. 1-7.
Dufort et al., "Abstract 4233: Generation of a Bicycle NK-TICA™, a novel NK cell engaging molecule designed to induce targeted tumor cytotoxicity", American Association for Cancer Research, Apr. 8, 2022, pp. 1-5.
Dufort, "Bicycles: Bispecific, Precision-guided NK Cell Activators for the Treatment of Solid Tumors", Innate Killer Summit, Mar. 29, 2023, 23 pages.
Eder et al., "Bicyclic Peptides as a New Modality for Imaging and Targeting of Proteins Overexpressed by Tumors", Cancer Res., Feb. 15, 2019, 79(4):841-852.
Eder et al., "OP337: A phage display derived stabilised bicyclic peptide targeting MMP-14 shows high imaging contrast in small animal PET imaging", In European Journal of Nuclear Medicine and Molecular Imaging, 2015, 42 (Suppl 1):S140-S141.
Evans et al., "Abstract CT253: Phase 1/2 study of the safety, pharmacokinetics, and preliminary clinical activity of BT7480 in patients with Nectin-4 associated advanced malignancies", American Association for Cancer Research Annual Meeting, Apr. 18, 2023, pp. 1-5.
Frigerio, "Expanding the Potential of ADCs: Bicyclic Peptide (Bicycle®) Toxin Conjugates May Offer Advancements Over Traditional ADCs", World ADC, Mar. 20, 2023, 28 pages.
Frigerio, "Targeting Tumors with Bicycle Conjugates", PEGS Boston, May 17, 2023, 31 pages.
Gelb et al., "Abstract A047: MT1-MMP Immunohistochemistry (IHC) analysis of tumor microarrays (TMAs) using a novel scoring system guides patient selection for BT1718 expansion cohorts", AACR-NCI-EORTC, Oct. 27, 2019, pp. 1-7.
GenBank Accession No. CZR33441.1, "uncharacterized protein FPRO_01747 [Fusarium proliferatum ET1]", National Center for Biotechnology Information, Retrieved from: https://www.ncbi.nlm.nih.gov/protein/1111492376, Dec. 6, 2016, 1 page.

(56) References Cited

OTHER PUBLICATIONS

Hacker et al., "Highly-constrained bicyclic scaffolds for the discovery of protease-stable peptides via mRNA display", ACS Chem. Biol., Mar. 17, 2017, 12(3):795-804.
Hadjicharalambous et al., "Investigating Penetration and Antimicrobial Activity of Vector Bicycle Conjugates", ACS Infectious Diseases, Jun. 12, 2024, 10(7):2381-2389.
Harrison et al., "Abstract 5144: BT1718, a novel bicyclic peptide-maytansinoid conjugate targeting MT1-MMP for the treatment of solid tumours: Design of bicyclic peptide and linker selection", AACR Annual meeting, Apr. 1, 2017, pp. 1-7.
Harrison et al., "Discovery and development of BT1718, a novel bicyclic peptidemaytansinoid conjugate targeting MT1-MMP for the treatment of solid tumours: In vitro and in vivo activities", PEGS, Apr. 30, 2017, 1 page.
Ho et al., "Expression of CD137 on Hodgkin and Reed-Sternberg Cells Inhibits T-cell Activation by Eliminating CD137 Ligand Expression", Cancer Research, Jan. 15, 2013, 73(2):652-661.
Hu et al., "Lessons Learned from Molecular Scaffold Analysis", Journal of Chemical Information and Modeling, 2011, 51(8):1742-1753.
Hurov et al., "Abstract 1340: BT7455, a fully synthetic Bicycle tumor-targeted immune cell agonist®, leads to potent EphA2-dependent CD137 agonism and robust anti-tumor efficacy", SITC, Nov. 10, 2022, pp. 1-6.
Hurov et al., "Abstract 3257: Activation of 4-1BB using multivalent and tumour targeted bicyclic peptides", American Association of Cancer Research, Apr. 2, 2019, pp. 1-4.
Hurov et al., "Abstract 3257: Activation of CD137 using multivalent and tumor targeted Bicyclic peptides", Cancer Res, Jul. 1, 2019, 79(13_Supplement):3257, 3 pages.
Hurov et al., "Abstract 700: EphA2/CD137 Bicycle® tumor-targeted immune cell agonists (TICAs™) induce tumor regressions, immunogenic memory, and reprogramming of the tumor immune microenvironment", SITC, Nov. 9, 2020, pp. 1-4.
Hurov et al., "Abstract P398: Activation of the T cell costimulatory protein CD137 using multivalent bicyclic peptides", SITC, Nov. 6, 2018, pp. 1-5.
Hurov et al., "Abstract P782: A novel fully synthetic dual targeted Nectin-4/4-1BB Bicycle® peptide induces tumor localized 4-1BB agonism", SITC, Nov. 9, 2019, pp. 1-6.
Hurov et al., "BT7480, a novel fully synthetic Bicycle tumor-targeted immune cell agonist™M (Bicycle TICATM) induces tumor localized CD137 agonism", Journal for Immuno Therapy of Cancer, 2021, 9(11):e002883, pp. 1-13.
Hurov et al., "Poster 1728: Nectin-4-dependent immune cell stimulation and anti-tumor efficacy by BT7480, a Nectin-4/CD137 Bicycle® tumor-targeted immune cell agonist (TICA™)", American Association of Cancer Research, Apr. 12, 2021, pp. 1-6.
Hurov, "BT7480, a novel and fully synthetic Bicycle tumor-targeted immune cell agonist®", Festival of Biologics, Nov. 4, 2022, 23 pages.
Kanakia et al., "Development of CD137 (4-1BB) receptor occupancy assay using fluorescently labeled Bicycles®", AACR Tumor Immunology & Immunotherapy, Oct. 19, 2020, 5 pages.
Keen, "A novel fully synthetic dual targeted Nectin-4/4-1BB Bicycle® peptide induces tumor localized 4-1BB agonism", SITC, Nov. 6-10, 2019, 19 pages.
Keen, "BT5528, an EphA2-targeting Bicycle® Toxin Conjugate", World ADC congress, Oct. 11, 2019, 24 pages.
Keen, "BT7480, a novel Nectin-4 dependent agonist of the immune cell costimulatory receptor CD137", AACR Annual Meeting, Apr. 10-15 and May 17-21, 2021, 23 pages.
Kristensson et al., "Novel Bicyclic Peptide Multimers Activate T Cell Costimulatory Protein CD137", ELRIG Drug Discovery, Oct. 9, 2018, pp. 1-7.
Kristensson et al., "Novel Bicyclic Peptide Multimers Activate T Cell Costimulatory Protein CD137", Promega Biologics, Jul. 18, 2018, pp. 1-7.
Kumara et al., "*Fusarium proliferatum*, an endophytic fungus from *Dysoxylum binectariferum* Hook.f, produces rohitukine, a chromane alkaloid possessing anti-cancer activity", Antonie van Leeuwenhoek, 2012, 101(2):323-329.
Lahdenranta et al., "Abstract 1356: Transcriptional profiling of Bicycle® tumor-targeted CD137 agonist-treated mouse tumors revealed an early and rapid activation of myeloid cells followed by infiltration of cytotoxic T cells into the tumor", SITC, Nov. 10, 2022, pp. 1-9.
Lahdenranta et al., "Abstract 5301: Tumor-targeted activation of CD137 using Bicycle® molecules: New insights into mechanism of action and discovery of BT7455, a clinical candidate for the treatment of EphA2-expressing cancers", American Association for Cancer Research Annual Meeting, Apr. 9, 2024, pp. 1-5.
Lahdenranta et al., "Abstract A067: BT7480, a synthetic Bicycle tumor-targeted immune cell agonist® (Bicycle TICA®), induces reprogramming of the tumor immune microenvironment through tumor localized CD137 agonism", CICON, Sep. 29, 2022, pp. 1-9.
Lahdenranta et al., "Poster 1319: Rapid accumulation of cytotoxic payload in tumor tissue drives BT5528 activity in tumor models", American Association of Cancer Research, Apr. 12, 2021, pp. 1-4.
Lahdenranta et al., "Poster 1724: Microinjection of Nectin-4/CD137 tumor-targeted immune cell agonist (TICA™) activates the local tumor microenvironment", American Association of Cancer Research, Apr. 12, 2021, pp. 1-4.
Lahdenranta et al., "Poster 706: BT7480, a fully synthetic tumor-targeted immune cell agonist (TICA™) induces tumor localized CD137 agonism and modulation of tumor immune microenvironment", SITC, Nov. 9, 2020, pp. 1-6.
Lau et al., "A penicillin-binding protein that can promote advanced-generation cephalosporin resistance and genome adaptation in the opportunistic pathogen Pseudomonas aeruginosa", International Journal of Antimicrobial Agents, 2020, 55(3):105896, pp. 1-8.
Loriot et al., "Abstract TPS4619: A phase 2/3 study of Bicycle® Toxin Conjugate zelenectide pevedotin (BT8009) targeting Nectin-4 in patients with locally advanced or metastatic urothelial cancer (1a/mUC) (Duravelo-2)", American Society of Clinical Oncology Annual Meeting, May 31-Jun. 4, 2024, 1 page.
Lowe, "Not Alphafold's Fault", blog—In the pipeline, Sep. 7, 2022, 6 pages.
Lowe, "The Good Sides and Bad Sides of Polar Compounds", blog—In the pipeline, Feb. 23, 2017, 15 pages.
Ludbrook, "Bicycle Toxin Conjugates to Target Solid Tumors", 3rd ADC Target Selection Summit, Dec. 6, 2023, 20 pages.
Luus et al., "Abstract 1832: EphA2-dependent CD137 agonism and anti-tumor efficacy by BT7455, a Bicycle tumor-targeted immune cell agonist®", American Association for Cancer Research Annual Meeting, Apr. 17, 2023, pp. 1-7.
McDonnell, "Bicycles for precision guided delivery", Boulder Peptide Symposium, Nov. 9, 2022, 29 pages.
McKean et al., "A Combined Phase I/II Study of BT8009 a Novel Bicycle® Toxin Conjugate with MMAE in Patients with Advanced Malignancies with Nectin-4", ASCO, Jun. 4, 2021, 1 page.
McKean et al., "BT8009-100 Phase I/II Study of Novel Bicyclic Peptide and MMAE Conjugate BT8009 in Patients with Advanced Malignancies Associated with Nectin-4 Expression", American Association for Cancer Research, Apr. 8-13, 2022, 17 pages.
McKean et al., "BT8009-100 Phase I/II Study of the Safety, Pharmacokinetics, & Preliminary Clinical Activity of BT8009 in Patients with Nectin-4 Expressing Advanced Malignancies", ESMO, Sep. 17, 2020, 1 page.
McKean, "A first in class phase I/II study of the novel bicyclic peptide and MMAE conjugate, BT5528, in patients with advanced malignancies associated with EphA2 expression", AACR-NCI-EORTC, Oct. 7-10, 2021, 19 pages.
Micoine et al., "A General Strategy for Ligation of Organic and Biological Molecules to Dawson and Keggin Polyoxotungstates", Organic Letters, Jul. 18, 2007, 9(20):3981-3984.
Mistry et al., "Abstract 15523: Establishing the preclinical/translational PK/PD relationship for BT7480, a Nectin4/CD137 Bicycle tumor-targeted immune cell agonist™ (Bicycle TICA™)", SITC, Nov. 12, 2021, pp. 1-5.

(56) References Cited

OTHER PUBLICATIONS

Mistry et al., "Synthesis of Bicycle® Peptides using Gold-mediated Cysteine Arylation", European Peptide Synthesis Conference, Mar. 7, 2023, 1 page.
Mudd et al., "Bicyclic Peptides for Positron Emission Tomography (PET) Imaging of MT1-MMP Expressing tumours", PEGS, Apr. 30, 2017, 1 page.
Mudd et al., "Discovery of BT8009: A Nectin-4 Targeting Bicycle Toxin Conjugate for the Treatment of Cancer", Journal of Medicinal Chemistry, 2022, 65(21): 14261-14970.
Mudd et al., "Gold-Mediated Multiple Cysteine Arylation for the Construction of Highly Constrained Bicycle Peptides", Bioconjugate Chemistry, 2022, 33(8):1441-1445.
Mudd et al., "Potent anti-tumor activity of a Lead-212 labelled MT1-MMP targeting Bicycle Radionuclide Conjugate™", Tides USA—Oligonucleotide, May 8, 2023, pp. 1-7.
Newman et al., "Anti-Infectives Drug Discovery at Bicycle Therapeutics", ESCMID, Oct. 11, 2022, 1 page.
Newman, "Characterisation of novel, noncovalent cyclic peptide (Bicycles®) inhibitors of PBP3s from important Gram-negative pathogens", ESCMID, Oct. 11, 2022, 18 pages.
Ngo et al., "Abstract 333: Activity of the erythropoietin-producing hepatocellular A2 receptor (EphA2) targeting Bicycle® Toxin Conjugate (BTC™) BCY6033 in EGFR inhibitor resistant non-small cell lung cancer (NSCLC) patient derived xenografts", American Association for Cancer Research, Apr. 8, 2022, pp. 1-6.
Nguyen, "Pancreatic Cancer", Merck Manual, Retrieved from: https://www.merckmanuals.com/home/digestive-disorders/tumors-of-the-digestive-system/pancreatic-cancer?query=pancreatic%20cancer, Mar. 2021, 4 pages.
Palma et al., "CD137 and CD137 Ligand Constitutively Coexpressed on Human T and B Leukemia Cells Signal Proliferation and Survival", Int J Cancer., 2004, 108(3):390-398.
Papadopoulos et al., "Abstract TPS2689: A Combined Phase I/II Study of a Novel Bicycle Tumor-targeted Immune Cell Agonist® BT7480 in Patients with Nectin-4 Associated Advanced Malignancies", ASCO, Jun. 6, 2022, 1 page.
Park et al., "Abstract 3756: Small Synthetic, Multivalent Bicyclic Peptides That Activate T Cell Costimulatory Protein CD137", American Association of Cancer Research, Apr. 14, 2018, pp. 1-9.
Park et al., "Abstract 3756: Small Synthetic, Multivalent Bicyclic Peptides That Activate T Cell Costimulatory Protein CD137", Cancer Res., Jul. 1, 2018, 78(13_Supplement):3756, 2 pages.
Park et al., "Abstract 3756: Small Synthetic, Multivalent Bicyclic Peptides That Activate T Cell Costimulatory Protein CD137", ELRIG Drug Discovery, Oct. 9, 2018, pp. 1-9.
Rajendran et al., "CD137 signaling in Hodgkin and Reed-Sternberg cell lines induces IL-13 secretion, immune deviation and enhanced growth", Oncoimmunology, 2016, 5(6):e1160188, 7 pages.
Repash et al., "BT7480, a novel fully synthetic tumor-targeted immune cell agonist (TICA™) induces tumor localized CD137 agonism", AACR Tumor Immunology & Immunotherapy, Oct. 19, 2020, 10 pages.
Rezvaya et al., "Abstract 1207: NKp46 engaging Bicycle NK-TICA® drives tumor targeted cytotoxicity", SITC, Nov. 10, 2022, 1 page.
Rhodes et al., "Bicyclic Peptides as Next-Generation Therapeutics", Chemistry—A European Journal, 2017, 23(52):12690-12703.
Rietschoten et al., "Abstract 268: Small Synthetic, Multivalent Bicyclic Peptides That Activate T Cell Costimulatory Protein CD137", 35th European Peptide Symposium, Aug. 1, 2018, 1 page.
Rigby et al., "Abstract 4479: BT8009: A bicyclic peptide toxin conjugate targeting Nectin-4 (PVRL4) displays efficacy in preclinical tumor models", Cancer Res, 2019, 79(13_Supplement):4479, 3 pages.
Rigby et al., "Abstract C061: BT8009, a Bicycle® Toxin Conjugate targeting Nectin-4, shows target selectivity, and efficacy in preclinical large and small tumor models", AACR-NCI-EORTC, Oct. 29, 2019, pp. 1-9.
Rigby et al., "BT8009; A Nectin-4 Targeting Bicycle® Toxin Conjugate for Treatment of Solid Tumors", Molecular Cancer Therapeutics, 2022, 21(12):1-27.
Rigby, "Abstract 4479: BT8009: A bicyclic peptide toxin conjugate targeting Nectin-4 (PVRL4) displays efficacy in preclinical tumour models", AACR Annual Meeting, Apr. 2, 2019, 10 pages.
Santos et al., "Abstract 35472: Characterization of Nectin-4 protein expression in non-small cell lung cancer patients", AACR-BC-EORTC, Oct. 13, 2023, pp. 1-4.
Shah et al., "Abstract A28: Establishment of an ex vivo tissue culture platform as a preclinical model to assess the mechanism of action of Bicycle® tumor-targeted immune cell agonists in Nsclc", AACR-BC-EORTC, Oct. 26, 2022, pp. 1-8.
Singh et al., "Protein Engineering Approaches in the Post-Genomic Era", Current Protein and Peptide Science, 2017, 18(4):1-11.
Skynner et al., "BT1718, a novel Bicycle Drug Conjugate® shows potent anti-tumor activity in diverse cell-derived and patient-derived tumor xenograft models", PEGS, Apr. 30, 2017, 1 page.
Solomons, "Organic Chemistry", 4th ed, 1988, p902, 3 pages.
Stanczuk et al., "Abstract 1388: Utility of humanized animal models for in vivo evaluation of NK-TICA®, novel Bicycle® tumor-targeted immune cell agonist® (Bicycle TICA®) designed to engage NK cells", SITC, Nov. 10, 2022, pp. 1-6.
Stanczuk et al., "Abstract 1826: Development of in vivo models for evaluation of Nk-TICA™, novel Bicycle® tumortargeted immune cell agonist® designed to engage NK cells", American Association for Cancer Research Annual Meeting, Apr. 17, 2023, pp. 1-6.
Su, "Key DMPK Attributes of BT7480, a Bicycle Tumor-targeted Immune Cell Agonist™ Targeting Nectin-4 and Agonizing CD137", NEDMDG symposium, May 31, 2023, 20 pages.
Teufel et al., "Abstract 4920: Bicyclic Peptides for Positron Emission Tomography (PET) Imaging of MT1-MMP Expressing Tumors", American Association of Cancer Research, Apr. 1, 2017, pp. 1-8.
Thornber, "Isosterism and Molecular Modification in Drug Design", Chem. Soc. Rev, 1979, 8(4):563-580.
Tiberghien, "Highlighting the Potential of Bicycle Conjugates to Target Solid Tumours", World ADC, Mar. 20, 2023, 24 pages.
Uhlenbroich et al., "Abstract 0000: NKp46 engaging Bicycle NK-TICA™ drives tumor targeted cytotoxicity", PEGS Boston, May 17, 2023, 1 page.
Uhlenbroich, "Bicycles—a modality for Tumor-Targeted Immune Cell Agonism", Antibody Engineering & Therapeutics, Jun. 12, 2023, 23 pages.
Upadhyaya et al., "Abstract 888: An integrative approach to optimize a synthetic EphA2-dependent CD137 agonist: Balancing potency, physiochemical properties, and pharmacokinetics to achieve robust anti-tumor activity", SITC, Nov. 12, 2021, pp. 1-7.
Upadhyaya et al., "Anticancer immunity induced by a synthetic tumor-targeted CD137 agonist", Journal for Immunotherapy of Cancer, 2021, 9(1):e001762, pp. 1-10.
Upadhyaya et al., "Discovery and Optimization of a Synthetic Class of Nectin-4-Targeted CD137 Agonists for Immuno-oncology", Molecular Cancer Therapeutics, 2022, 65:9858-9872.
Upadhyaya, "Activation of CD137 using multivalent and tumour targeted bicyclic peptides", Peptide Congress, Retrieved from: https://www.bicycletherapeutics.com/wp-content/uploads/PU_2019-Peptide-Congress_publication.pdf, Apr. 2019, 25 pages.
Valko et al., "Application of biomimetic HPLC to estimate lipophilicity, protein and phospholipid binding of potential peptide therapeutics", ADMET and DMPK, 2018, 6(2):162-175
Wagstaff et al., "An Assay for Periplasm Entry Advances the Development of Chimeric Peptide Antibiotics", ACS Infectious Diseases, 2020, 6(9):2355-2361.
Wallack et al., "Abstract P05: Investigating soluble Nectin-4 and EphA2 as cancer biomarkers in plasma", Bio-IT World, May 23, 2023, pp. 1-6.
Walsh et al., "Abstract 5807: Bicycle Toxin Conjugates® for the treatment of solid tumors", American Association for Cancer Research Annual Meeting, Apr. 9, 2024, pp. 1-7.
Wang et al., "Comprehensive Surfaceome Profiling to Identify and Validate Novel Cell-Surface Targets in Osteosarcoma", Molecular Cancer Therapeutics, Jun. 2022, 21(6):903-913.

(56) References Cited

OTHER PUBLICATIONS

Wang et al., "Integrative surfaceome profiling identifies immunotherapeutic targets in osteosarcoma and preclinical testing of BT1769, an MT1-MMP-targeted Bicycle® toxin conjugate, in osteosarcoma by the Pediatric Preclinical Testing Consortium (PPTC)", AACR Annual Meeting, Apr. 10-15 and May 17-21, 2021, 15 pages.
Xu et al., "The application of PK/PD modelling in the clinical development of BT5528—a novel toxin delivery platform", ACoP, Oct. 30-Nov. 2, 2022, 21 pages.
Yampolsky et al., "The Exchangeability of Amino Acids in Proteins", Genetics, Aug. 2005, 170(4):1459-1472.
Zapun et al., "Penicillin-binding proteins and Beta-lactam resistance", FEMS Microbiology Reviews, 2008, 32(2):361-385.
Zhang et al., "Characterization and application of three novel monoclonal antibodies against human 4-1BB: distinct epitopes of human 4-1BB on lung tumor cells and immune cells", Tissue Antigens, 2007, 70(6):470-479.
Zhang et al., "Propagated Perturbations from a Peripheral Mutation Show Interactions Supporting WW Domain Thermostability", Structure, Nov. 6, 2018, 26(11):1474-1485.
U.S. Appl. No. 18/742,691, Chen, filed on Jun. 13, 2024.
U.S. Appl. No. 18/906,616, Beswick et al., filed on Oct. 4, 2024.

\* cited by examiner

SEQUENCE LISTING

```
<160> NUMBER OF SEQ ID NOS: 17

<210> SEQ ID NO 1
<211> LENGTH: 12
<212> TYPE: PRT
<213> ORGANISM: Artificial Sequence
<220> FEATURE:
<223> OTHER INFORMATION: synthetic

<400> SEQUENCE: 1

Cys Met Val Cys His Met Met Glu Asp Gly Thr Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic

<400> SEQUENCE: 2

Cys Ile Glu Cys Tyr Ile Met Glu Asp Gly Thr Cys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: synthetic

<400> SEQUENCE: 3

Cys Glu Glu Cys Leu Thr Leu Glu Asp Gly Thr Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: synthetic

<400> SEQUENCE: 4

Cys Glu Glu Cys Phe Arg Leu Glu Asp Gly Thr Cys
1               5                   10

<210> SEQ ID NO 5
<211> LENGTH: 12
```

```
<212> TYPE: PRT
<213> ORGANISM: Artificial Sequence
<220> FEATURE:
<223> OTHER INFORMATION: synthetic

<400> SEQUENCE: 5

Cys Trp Asp Cys Phe Met Met Glu Asp Gly Thr Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(7)
<223> OTHER INFORMATION: Xaa represents Nle

<400> SEQUENCE: 6

Cys Trp Asp Cys Phe Xaa Xaa Glu Asp Gly Thr Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: Xaa represents Nle

<400> SEQUENCE: 7

Cys Trp Asp Cys Phe Xaa Met Glu Asp Gly Thr Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa represents Nle

<400> SEQUENCE: 8

Cys Trp Asp Cys Phe Met Xaa Glu Asp Gly Thr Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(7)
<223> OTHER INFORMATION: Xaa represents Nle

<400> SEQUENCE: 9

Cys Trp Asp Cys Phe Xaa Xaa Glu Asp Gly Thr Cys
1               5                   10
```

-continued

```
<210> SEQ ID NO 10
<211> LENGTH: 12
<212> TYPE: PRT
<213> ORGANISM: Artificial Sequence
<220> FEATURE:
<223> OTHER INFORMATION: synthetic

<400> SEQUENCE: 10

Cys Arg Glu Cys Tyr Met Met Glu Asp Gly Thr Cys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: synthetic

<400> SEQUENCE: 11

Cys Ser Glu Cys Tyr Met Met Glu Asp Gly Thr Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: synthetic

<400> SEQUENCE: 12

Cys Met Glu Cys Tyr Met Met Glu Asp Gly Thr Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: synthetic

<400> SEQUENCE: 13

Cys Leu Glu Cys Asn Met Met Glu Asp Gly Thr Cys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Xaa represents Nle
<220> FEATURE:
<221> NAME/KEY: MISC_FEATURE
<222> LOCATION: (6)..(7)
<223> OTHER INFORMATION: Xaa represents Nle

<400> SEQUENCE: 14

Cys Xaa Val Cys His Xaa Xaa Glu Asp Gly Thr Cys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: synthetic
```

```
<220> FEATURE:
<221> NAME/KEY: MISC_FEATURE
<222> LOCATION: (2)..(3)
<223> OTHER INFORMATION: Xaa represents any amino acid
<220> FEATURE:
<221> NAME/KEY: MISC_FEATURE
<222> LOCATION: (5)..(7)
<223> OTHER INFORMATION: Xaa represents any amino acid

<400> SEQUENCE: 15

Cys Xaa Xaa Cys Xaa Xaa Xaa Glu Asp Gly Thr Cys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(3)
<223> OTHER INFORMATION: Xaa represents any amino acid
<220> FEATURE:
<221> NAME/KEY: MISC_FEATURE
<222> LOCATION: (5)..(6)
<223> OTHER INFORMATION: Xaa represents any amino acid
<220> FEATURE:
<221> NAME/KEY: MISC_FEATURE
<222> LOCATION: (7)..(7)
<223> OTHER INFORMATION: Xaa represents L, M or Nle

<400> SEQUENCE: 16

Cys Xaa Xaa Cys Xaa Xaa Xaa Glu Asp Gly Thr Cys
1               5                   10

<210> SEQ ID NO 17
<211> LENGTH: 25
<212> TYPE: PRT
<213> ORGANISM: Artificial
<220> FEATURE:
<223> OTHER INFORMATION: synthetic

<400> SEQUENCE: 17

Ala Cys Met Val Cys His Met Met Glu Asp Gly Thr Cys Ala Gly Ala
1               5                   10                  15

Ser Pro Ala Ala Pro Ser Ala Pro Pro
            20                  25
```

BICYCLIC PEPTIDE LIGANDS SPECIFIC FOR PSMA

CROSS-REFERENCE TO RELATED APPLICATIONS

This application is the national stage of International Patent Application No. PCT/GB2019/053536, filed on Dec. 13, 2019, which claims the benefit of United Kingdom Application No. 1820325.7, filed on Dec. 13, 2018, the entire contents of each of which are incorporated herein by reference.

SEQUENCE LISTING

The instant application contains a Sequence Listing in ASCII format which has been submitted electronically and is hereby incorporated by reference in its entirety. Said copy, created on Dec. 16, 2024, is named Bicycle_183877_SL2.txt and is 14,222 bytes in size.

FIELD OF THE INVENTION

The present invention relates to polypeptides which are covalently bound to molecular scaffolds such that two or more peptide loops are subtended between attachment points to the scaffold. In particular, the invention describes peptides which are high affinity binders of prostrate-specific membrane antigen (PSMA). The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by PSMA.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å2; Wu et al. (2007), Science 330, 1066-71), a cyclic peptide with the Arg-Gly-Asp motif binding to integrin αVb3 (355 Å2) (Xiong et al. (2002), Science 296 (5565), 151-5) or the cyclic peptide inhibitor upain-1 binding to urokinase-type plasminogen activator (603 Å2; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8 (MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO 2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule scaffold.

SUMMARY OF THE INVENTION

According to a first aspect of the invention, there is provided a peptide ligand specific for PSMA comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold.

According to a further aspect of the invention, there is provided a drug conjugate comprising a peptide ligand as defined herein conjugated to one or more effector and/or functional groups.

According to a further aspect of the invention, there is provided a pharmaceutical composition comprising a peptide ligand or a drug conjugate as defined herein in combination with one or more pharmaceutically acceptable excipients.

According to a further aspect of the invention, there is provided a peptide ligand or drug conjugate as defined herein for use in preventing, suppressing or treating a disease or disorder mediated by PSMA.

DETAILED DESCRIPTION OF THE INVENTION

In one embodiment, said loop sequences comprise 2 or 7 amino acids.

In a further embodiment, said loop sequences comprise three cysteine residues separated by two loop sequences one of which consists of 2 amino acids and the other of which consists of 7 amino acids.

In one embodiment, the peptide ligand comprises an amino acid sequence selected from:

(SEQ ID NO: 15)
$C_i$-X-X-$C_{ii}$-X-X-X-X-E-D-G-T-$C_{iii}$;

wherein X represents any amino acid residue and $C_i$, $C_{ii}$ and $C_{iii}$ represent first, second and third cysteine residues, respectively or a pharmaceutically acceptable salt thereof.

In one embodiment, the peptide ligand comprises an amino acid sequence selected from:

$C_i$-X-X-$C_{ii}$-X-X-L/M/Nle-E-D-G-T-$C_{iii}$; (SEQ ID NO: 16)

wherein X represents any amino acid residue, Nle represents norleucine and $C_i$, $C_{ii}$ and $C_{iii}$ represent first, second and third cysteine residues, respectively or a pharmaceutically acceptable salt thereof.

In a further embodiment, the peptide ligand of $C_i$-X-X-$C_{ii}$-X-X-X-E-D-G-T-$C_{iii}$ (SEQ ID NO: 15) or $C_i$-X-X-$C_{ii}$-X-X-L/M/Nle-E-D-G-T-$C_{iii}$ (SEQ ID NO: 16) comprises an amino acid sequence selected from any one of SEQ ID NOS: 1 to 14:

$C_i$MV$C_{ii}$HMMEDGT$C_{iii}$; (SEQ ID NO: 1)

$C_i$IE$C_{ii}$YIMEDGT$C_{iii}$; (SEQ ID NO: 2)

$C_i$EE$C_{ii}$LTLEDGT$C_{iii}$; (SEQ ID NO: 3)

$C_i$EE$C_{ii}$FRLEDGT$C_{iii}$; (SEQ ID NO: 4)

$C_i$WD$C_{ii}$FMMEDGT$C_{iii}$; (SEQ ID NO: 5)

$C_i$WD$C_{ii}$F(Nle)(Nle)EDGT$C_{iii}$; (SEQ ID NO: 6)

$C_i$WD$C_{ii}$F(Nle)MEDGT$C_{iii}$; (SEQ ID NO: 7)

$C_i$WD$C_{ii}$FM (SEQ ID NO: 8)

$C_i$WD$C_{ii}$F(Nle)(Nle)EDGT$C_{iii}$; (SEQ ID NO: 9)

$C_i$RE$C_{ii}$YMMEDGT$C_{iii}$; (SEQ ID NO: 10)

$C_i$SE$C_{ii}$YMMEDGT$C_{iii}$; (SEQ ID NO: 11)

$C_i$ME$C_{ii}$YMMEDGT$C_{iii}$; (SEQ ID NO: 12)

$C_i$LE$C_{ii}$NMMEDGT$C_{iii}$; and (SEQ ID NO: 13)

$C_i$(Nle)V$C_{ii}$H(Nle)(Nle)EDGT$C_{iii}$ (SEQ ID NO: 14)

wherein $C_i$, $C_{ii}$ and $C_{ii}$ represent first, second and third cysteine residues, respectively and Nle represents norleucine, or a pharmaceutically acceptable salt thereof.

In a further embodiment, the peptide ligand of $C_i$-X-X-$C_{ii}$-X-X-X-E-D-G-T-$C_{iii}$ (SEQ ID NO: 15) or $C_i$-X-X-$C_i$-X-X-L/M/Nle-E-D-G-T-$C_{ii}$ (SEQ ID NO: 16) comprises an amino acid sequence selected from:

A-(SEQ ID NO: 1)-A (herein referred to as 21-31-N002); (SEQ ID NO: 18);

Ac-(SEQ ID NO: 1) (herein referred to as 21-31-N003); (SEQ ID NO: 40);

A (SEQ ID NO: 1)-AGASPAAPSAPP (herein referred to as 21-31-N004; SEQ ID NO: 17);

(SEQ ID NO: 2)-A (herein referred to as 21-31-01-N001); (SEQ ID NO: 19);

(SEQ ID NO: 3)-A (herein referred to as 21-31-02-N001); (SEQ ID NO: 20);

(SEQ ID NO: 4)-A (herein referred to as 21-31-03-N001); (SEQ ID NO: 21);

EV-(SEQ ID NO: 5)-A (herein referred to as 21-31-04-T01-N001); (SEQ ID NO: 22);

(D-E)V-(SEQ ID NO: 5)-A-$Sar_6$-K (herein referred to as 21-31-04-T01-N002); (SEQ ID NO: 23);

β-Ala-$Sar_5$-EV-(SEQ ID NO: 5) (herein referred to as 21-31-04-T01-N003); (SEQ ID NO: 24);

Ac-(D-E)-V-(SEQ ID NO: 5)-A-$Sar_6$-K—Ac (herein referred to as 21-31-04-T01-N004); (SEQ ID NO: 25);

Ac-(D-E)-V-(SEQ ID NO: 6)-A-$Sar_6$-K (herein referred to as 21-31-04-T01-N005); (SEQ ID NO: 26);

Ac-(D-E)-V-(SEQ ID NO: 5)-A-$Sar_6$-(D-Lys) (herein referred to as 21-31-04-T01-N007); (SEQ ID NO: 27);

Ac-(D-E)-V-(SEQ ID NO: 7)-A-$Sar_6$-(D-Lys) (herein referred to as 21-31-04-T01-N008); (SEQ ID NO: 28);

Ac-(D-E)-V-(SEQ ID NO: 8)-A-$Sar_6$-(D-Lys) (herein referred to as 21-31-04-T01-N009); (SEQ ID NO: 29);

Ac-(D-E)-V-(SEQ ID NO: 9)-A-$Sar_6$-(D-Lys) (herein referred to as 21-31-04-T01-N010); (SEQ ID NO: 30);

SV-(SEQ ID NO: 10)-A (herein referred to as 21-31-07-T01-N001); (SEQ ID NO: 31);

F-(SEQ ID NO: 11)-A (herein referred to as 21-31-11-T01-N001); (SEQ ID NO: 32);

L-(SEQ ID NO: 12)-A (herein referred to as 21-31-12-T01-N001); (SEQ ID NO: 33);

(D-Val)-(SEQ ID NO: 13)-A-$Sar_6$-K (herein referred to as 21-31-14-T01-N002); (SEQ ID NO: 34);

β-Ala-$Sar_5$-V-(SEQ ID NO: 13) (herein referred to as 21-31-14-T01-N003); (SEQ ID NO: 35);

Ac-(SEQ ID NO: 1)-A-$Sar_6$-K (herein referred to as 21-31-N005); (SEQ ID NO: 36);

β-Ala-$Sar_5$-A-(SEQ ID NO: 1) (herein referred to as 21-31-N006); (SEQ ID NO: 37);

Ac-(SEQ ID NO: 14)-A-$Sar_6$-K (herein referred to as 21-31-N007); (SEQ ID NO: 38); and β-Ala-$Sar_5$-A-(SEQ ID NO: 14) (herein referred to as 21-31-N008) (SEQ ID NO: 39).

In a further embodiment, the peptide ligand of $C_i$-X-X-$C_{ii}$-X-X-X-E-D-G-T-$C_{iii}$ (SEQ ID NO: 15) or $C_i$-X-X-$C_{ii}$-X-X-L/M/Nle-E-D-G-T-$C_{iii}$ (SEQ ID NO: 16) comprises an amino acid sequence selected from:

EV-(SEQ ID NO: 5)-A (herein referred to as 21-31-04-T01-N001) (SEQ ID NO: 22);

Ac-(D-E)-V-(SEQ ID NO: 8)-A-$Sar_6$-(D-Lys) (herein referred to as 21-31-04-T01-N009) (SEQ ID NO: 29);

F-(SEQ ID NO: 11)-A (herein referred to as 21-31-11-T01-N001) (SEQ ID NO: 32); and L-(SEQ ID NO: 12)-A (herein referred to as 21-31-12-T01-N001) (SEQ ID NO: 33). The peptide ligands of this embodiment demonstrated superior PSMA binding as shown herein in Table 1.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) 4th ed., John Wiley & Sons, Inc.), which are incorporated herein by reference.

Nomenclature

Numbering

When referring to amino acid residue positions within the peptides of the invention, cysteine residues ($C_i$, $C_{ii}$ and $C_{iii}$) are omitted from the numbering as they are invariant, therefore, the numbering of amino acid residues within the peptides of the invention is referred to as below:

(SEQ ID NO: 1)
$-C_i-M_1-V_2-C_{ii}-H_3-M_4-M_5-E_6-D_7-G_8-T_9-C_{iii}-$.

For the purpose of this description, all bicyclic peptides are assumed to be cyclised with TBMB (1,3,5-tris(bromomethyl)benzene) yielding a tri-substituted 1,3,5-trismethylbenzene structure. Cyclisation with TBMB occurs on $C_i$, $C_{ii}$, and $C_{iii}$.

Molecular Format

N- or C-terminal extensions to the bicycle core sequence are added to the left or right side of the sequence, separated by a hyphen. For example, an N-terminal βAla-Sar10-Ala tail would be denoted as:

(SEQ ID NO: 41)
βAla-Sar10-A-.

Inversed Peptide Sequences

In light of the disclosure in Nair et al (2003) J Immunol 170 (3), 1362-1373, it is envisaged that the peptide sequences disclosed herein would also find utility in their retro-inverso form. For example, the sequence is reversed (i.e. N-terminus becomes C-terminus and vice versa) and their stereochemistry is likewise also reversed (i.e. D-amino acids become L-amino acids and vice versa).

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as $C_i$, $C_{ii}$ and $C_{iii}$), and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes;

An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent; and Selectivity. Certain peptide ligands of the invention demonstrate good selectivity over other membrane antigens.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (+)-DL-lactic), lactobionic, maleic, malic, (−)-L-malic, malonic, (+)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH^{4+}$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the peptides of the invention contain an amine function, these may form quaternary ammonium salts, for example by reaction with an alkylating agent according to methods well known to the skilled person. Such quaternary ammonium compounds are within the scope of the peptides of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as C)) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group (the group referred to herein as $C_{iii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102 (2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons. (for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio) isotope-labeled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio) isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^{2}H$ (D) and $^{3}H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, sulfur, such as $^{35}S$, copper, such as $^{64}Cu$, gallium, such as $^{67}Ga$ or $^{68}Ga$, yttrium, such as $^{9}Y$ and lutetium, such as $^{177}Lu$, and Bismuth, such as $^{213}Bi$.

Certain isotopically-labelled peptide ligands of the invention, for example, those incorporating a radioactive isotope, are useful in drug and/or substrate tissue distribution studies, and to clinically assess the presence and/or absence of the PSMA target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}H$ (T), and carbon-14, i.e. $^{14}C$, are particularly useful for this purpose in view of their ease of incorporation and ready means of detection.

Substitution with heavier isotopes such as deuterium, i.e. $^{2}H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labeled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of tris(bromomethyl)benzene, especially 1,3,5-tris(bromomethyl)benzene ('TBMB'), or a derivative thereof.

In one embodiment, the molecular scaffold is 2,4,6-tris (bromomethyl) mesitylene. This molecule is similar to 1,3, 5-tris(bromomethyl)benzene but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromoethylbenzene (the scaffold reactive group exemplified by TBMB) or iodoacetamide. Other scaffold reactive groups that are used to selectively couple compounds to cysteines in proteins are maleimides, αβ unsaturated carbonyl containing compounds and α-halomethylcarbonyl containing compounds. Examples of maleimides which may be used as molecular scaffolds in the invention include: tris-(2-maleimidoethyl)amine, tris-(2- maleimidoethyl)benzene, tris-(maleimido)benzene. An example of an αβ unsaturated carbonyl containing compound is 1,1',1''-(1,3,5-triazinane-1,3,5-triyl)triprop-2-en-1-one (TATA) (Angewandte Chemie, International Edition (2014), 53(6), 1602-1606). An example of an xx-halomethylcarbonyl containing compound is N,N',N''-(benzene-1,3,5-triyl)tris(2-bromoacetamide). Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Effector and Functional Groups

According to a further aspect of the invention, there is provided a drug conjugate comprising a peptide ligand as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains.

An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a $t\beta$ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a $t\beta$ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of *Drosophila* (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from *Drosophila* Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

In one embodiment, a peptide ligand-effector group according to the invention has a $t\beta$ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a $t\beta$ half life in the range 12 to 60 hours. In a further embodiment, it will have a $t\beta$ half-life of a day or more. In a further embodiment still, it will be in the range 12 to 26 hours.

In one particular embodiment of the invention, the functional group is selected from a metal chelator, which is suitable for complexing metal radioisotopes of medicinal relevance.

Possible effector groups also include enzymes, for instance such as carboxypeptidase G2 for use in enzyme/prodrug therapy, where the peptide ligand replaces antibodies in ADEPT.

In one particular embodiment of the invention, the functional group is selected from a drug, such as a cytotoxic agent for cancer therapy. Suitable examples include: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including *vinca* alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin, calicheamicins, and others.

In one further particular embodiment of the invention, the cytotoxic agent is selected from maytansinoids (such as DM1) or monomethyl auristatins (such as MMAE).

DM1 is a cytotoxic agent which is a thiol-containing derivative of maytansine and has the following structure:

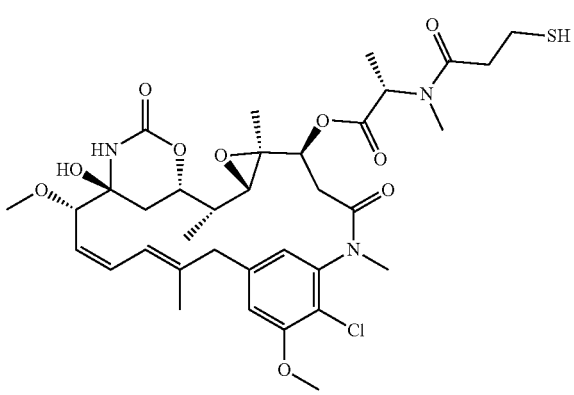 [SMILES: COc1cc2cc(c1Cl)N(C)C(=O)C[C@H](OC(=O)[C@H](C)N(C)C(=O)CCS)[C@]1(C)O[C@H]1[C@H](C)[C@@H]1C[C@@](O)(NC(=O)O1)[C@@H](OC)/C=C\C=C(/C)C2]

Monomethyl Auristatin E (MMAE) is a Synthetic Antineoplastic Agent and has the Following Structure:

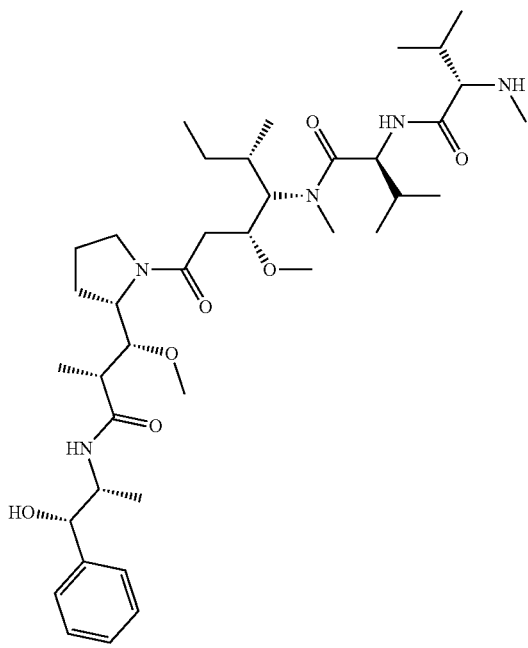

In one embodiment, the cytotoxic agent is linked to the bicyclic peptide by a cleavable bond, such as a disulphide bond or a protease sensitive bond. In a further embodiment, the groups adjacent to the disulphide bond are modified to control the hindrance of the disulphide bond, and by this the rate of cleavage and concomitant release of cytotoxic agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on either the targeting entity (here, the bicyclic peptide) or toxin side of the molecular construct.

In one embodiment, the cytotoxic agent and linker is selected from any combinations of those described in WO 2016/067035 (the cytotoxic agents and linkers thereof are herein incorporated by reference).

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio) conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TBMB) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand or a drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used.

For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as PSMA binding agents.

Prostate-specific membrane antigen (PSMA) (also known as Glutamate carboxypeptidase II (GCPII), N-acetyl-L-aspartyl-L-glutamate peptidase I (NAALADase I) and NAAG peptidase) is an enzyme that in humans is encoded by the FOLH1 (folate hydrolase 1) gene. Human GCPII contains 750 amino acids and weighs approximately 84 kDa.

Human PSMA is highly expressed in the prostate, roughly a hundred times greater than in most other tissues. In some prostate cancers, PSMA is the second-most upregulated gene product, with an 8- to 12-fold increase over levels in noncancerous prostate cells. Because of this high expression, PSMA is being developed as potential biomarker for therapy and imaging of some cancers. In human prostate cancer, the higher expressing tumors are associated with quicker time to progression and a greater percentage of patients suffering relapse.

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

According to a further aspect of the invention, there is provided a peptide ligand or a drug conjugate as defined herein, for use in preventing, suppressing or treating a disease or disorder mediated by PSMA.

According to a further aspect of the invention, there is provided a method of preventing, suppressing or treating a disease or disorder mediated by PSMA, which comprises administering to a patient in need thereof an effector group and drug conjugate of the peptide ligand as defined herein.

In one embodiment, the PSMA is mammalian PSMA. In a further embodiment, the mammalian PSMA is human PSMA.

In one embodiment, the disease or disorder mediated by PSMA is selected from: cancer, neuropathic and inflammatory pain, head injury, stroke, schizophrenia, diabetic neuropathy, drug addiction, amyotrophic lateral sclerosis and neurodegenerative diseases such as Parkinson's disease and Huntington's disease.

In a further embodiment, the disease or disorder mediated by PSMA is selected from cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythemia vera, essential thrombocythemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In a further embodiment, the cancer is selected from cancer of the prostate, breast, kidney and colon.

In a yet further embodiment, the cancer is selected from cancer of the prostate and breast.

In a yet further embodiment, the cancer is selected from cancer of the prostate.

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Materials and Methods

Peptide Synthesis

Peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with appropriate side chain protecting groups: where applicable standard coupling conditions were used in each case, followed by deprotection using standard methodology. Peptides were purified using HPLC and following isolation they were modified with 1,3,5-tris(bromomethyl) benzene (TBMB, Sigma). For this, linear peptide was diluted with $H_2O$ up to ~35 mL, ~500 µL of 100 mM TBMB in acetonitrile was added, and the reaction was initiated with 5 mL of 1 M $NH_4HCO_3$ in $H_2O$. The reaction was allowed to proceed for ~30-60 min at RT, and lyophilised once the reaction had completed (judged by MALDI). Following lyophilisation, the modified peptide was purified as above, while replacing the Luna C8 with a Gemini C18 column (Phenomenex), and changing the acid to 0.1% trifluoroacetic acid. Pure fractions containing the correct TMB-modified material were pooled, lyophilised and kept at −20° C. for storage.

All amino acids, unless noted otherwise, were used in the L-configurations.

BIOLOGICAL DATA

PSMA Binding and Enzyme Inhibition Assays

PSMA binding was measured using the fluorescence polarization assay methodology described in Shen et al (2013) PLOS ONE 8(7), 668339 and PSMA enzyme inhibition was measured using the methodology described in WO 2009/070302.

The peptide ligands of the invention were tested in the above mentioned PSMA binding and enzyme inhibition assays and the results are shown in Table 1:

TABLE 1

Biological Assay Data for Peptide Ligands of the Invention

| Name | Sequence | FP(h) ki (nM) | Enzyme inhibition IC50 (nM) |
|---|---|---|---|
| 21-31-N002 | ACMVCHMMEDGTCA (A-(SEQ ID NO: 1)-A) (SEQ ID NO: 18) | 40 | 695 |
| 21-31-N003 | Ac-CMVCHMMEDGTC (Ac-(SEQ ID NO: 1)) (SEQ ID NO: 40) | 182 | 5938 |
| 21-31-N004 | ACMVCHMMEDGTCA GASPAAPSAPP ((SEQ ID NO: 1)-AGASPAAPSAPP) (SEQ ID NO: 17) | 95.5 | |
| 21-31-01-N001 | CIECYIMEDGTCA ((SEQ ID NO: 2)-A) (SEQ ID NO: 19) | 70.0 | |
| 21-31-02-N001 | CEECLTLEDGTCA ((SEQ ID NO: 3)-A) (SEQ ID NO: 20) | 28.0 | |
| 21-31-03-N001 | CEECFRLEDGTCA ((SEQ ID NO: 4)-A) (SEQ ID NO: 21) | 36.5 | |
| 21-31-04-T01-N001 | EVCWDCFMMEDGTCA (EV-(SEQ ID NO: 5)-A) (SEQ ID NO: 22) | 2.2 | |
| 21-31-04-T01-N002 | (D-E)VCWDCFMMEDGTCA-Sar6-K ((D-E)V-(SEQ ID NO: 5)-A-Sar$_6$-K) (SEQ ID NO: 23) | 25.8 | |
| 21-31-04-T01-N003 | (B-Ala)-Sar5-EVCWDCFMMEDGTC (β-Ala-Sar$_5$-EV-(SEQ ID NO: 5)) (SEQ ID NO: 24) | 162.6 | |
| 21-31-04-T01-N004 | Ac-(D-E)VCWDCFMMEDGTCA-Sar6-K(Ac) (Ac-(D-E)-V-(SEQ ID NO: 5)-A-Sar$_6$-K-Ac) (SEQ ID NO: 25) | 18.3 | |
| 21-31-04-T01-N005 | Ac-(D-E)VCWDCF(Nle)(Nle)EDGTCA-Sar6-K (Ac-(D-E)-V-(SEQ ID NO: 6)-A-Sar$_6$-K) (SEQ ID NO: 26) | 38.5 | |
| 21-31-04-T01-N007 | Ac-(D-E)VCWDCFMMEDGTCA-Sar6-(D-K) (Ac-(D-E)-V-(SEQ ID NO: 5)-A-Sar$_6$-(D-Lys)) (SEQ ID NO: 27) | 30.0 | |
| 21-31-04-T01-N008 | Ac-(D-E)VCWDCF(Nle)MEDGTCA-Sar6-(D-K) (Ac-(D-E)-V-(SEQ ID NO: 7)-A-Sar$_6$-(D-Lys)) (SEQ ID NO: 28) | 82.0 | |
| 21-31-04-T01-N009 | Ac-(D-E)VCWDCFM(Nle)EDGTCA-Sar6-(D-K) (Ac-(D-E)-V-(SEQ ID NO: 8)-A-Sar$_6$-(D-Lys)) (SEQ ID NO: 29) | 5.1 | |
| 21-31-04-T01-N010 | Ac-(D-E)VCWDCF(Nle)(Nle)EDGTCA-Sar6-(D-K) (Ac-(D-E)-V-(SEQ ID NO: 9)-A-Sar$_6$-(D-Lys)) (SEQ ID NO: 30) | 55.0 | |
| 21-31-07-T01-N001 | SVCRECYMMEDGTCA (SV-(SEQ ID NO: 10)-A) (SEQ ID NO: 31) | 13 | |
| 21-31-11-T01-N001 | FCSECYMMEDGTCA (F-(SEQ ID NO: 11)-A) (SEQ ID NO: 32) | 6 | |
| 21-31-12-T01-N001 | LCMECYMMEDGTCA (L-(SEQ ID NO: 12)-A) (SEQ ID NO: 33) | 7.6 | |
| 21-31-14-T01-N002 | (D-V)CLECNMMEDGTCA-Sar6-K ((D-Val)-(SEQ ID NO: 13)-A-Sar$_6$-K) (SEQ ID NO: 34) | 1487.0 | |
| 21-31-14-T01-N003 | (B-Ala)-Sar5-VCLECNMMEDGTC (β-Ala-Sar$_5$-V-(SEQ ID NO: 13)-A-Sar$_6$-K) (SEQ ID NO: 35) | 512.5 | |
| 21-31-N005 | Ac-CMVCHMMEDGTCA-Sar6-K (Ac-(SEQ ID NO: 1)-A-Sar$_6$-K) (SEQ ID NO: 36) | 383.5 | |
| 21-31-N006 | (B-Ala)-Sar5-ACMVCHMMEDGTC (β-Ala-Sar$_5$-A-(SEQ ID NO: 1)) (SEQ ID NO: 37) | 595.5 | |

TABLE 1-continued

Biological Assay Data for Peptide Ligands of the Invention

| Name | Sequence | FP(h) ki (nM) | Enzyme inhibition IC50 (nM) |
|---|---|---|---|
| 21-31-N007 | Ac-C(Nle)VCH(Nle)(Nle)EDGTCA-Sar6-K (Ac-(SEQ ID NO: 14)-A-Sar$_6$-K) (SEQ ID NO: 38) | 296.0 | |
| 21-31-N008 | (β-Ala)-Sar5-AC(Nle)VCH(Nle)(Nle)EDGTC (β-Ala-Sar$_5$-A-(SEQ ID NO: 14)) (SEQ ID NO: 39) | 1364.5 | |

The invention claimed is:

1. A drug conjugate comprising a peptide ligand, or a pharmaceutically acceptable salt thereof, conjugated to one or more effector and/or functional groups, wherein the peptide ligand is specific for prostate specific membrane antigen (PSMA) and consists of $C_i$-X-X-$C_{ii}$-X-X-X-E-D-G-T-$C_{iii}$ (SEQ ID NO: 15) wherein X is any amino acid and wherein $C_i$, $C_{ii}$, and $C_{iii}$ form covalent bonds with a molecular scaffold to form at least two polypeptide loops.

2. The drug conjugate of claim 1, wherein the peptide ligand consists of:

$$C_i\text{-X-X-}C_{ii}\text{-X-X-L/M/Nle-E-D-G-T-}C_{iii} \quad \text{(SEQ ID NO: 16)}$$

wherein X represents any amino acid residue.

3. The drug conjugate of claim 1, wherein the peptide ligand is selected from the group consisting of:

$C_i$MVC$_{ii}$HMMEDGTC$_{iii}$; (SEQ ID NO: 1)

$C_i$IEC$_{ii}$YIMEDGTC$_{iii}$; (SEQ ID NO: 2)

$C_i$EEC$_{ii}$LTLEDGTC$_{iii}$; (SEQ ID NO: 3)

$C_i$EEC$_{ii}$FRLEDGTC$_{iii}$; (SEQ ID NO: 4)

$C_i$WDC$_{ii}$FMMEDGTC$_{iii}$; (SEQ ID NO: 5)

$C_i$WDC$_{ii}$F(Nle)(Nle)EDGTC$_{iii}$; (SEQ ID NO: 6)

$C_i$WDC$_{ii}$F(Nle)MEDGTC$_{iii}$; (SEQ ID NO: 7)

-continued

C$_i$WDC$_{ii}$FM (SEQ ID NO: 8)

C$_i$WDC$_{ii}$F(Nle)(Nle)EDGTC$_{iii}$; (SEQ ID NO: 9)

C$_i$REC$_{ii}$YMMEDGTC$_{iii}$; (SEQ ID NO: 10)

C$_i$SEC$_{ii}$YMMEDGTC$_{iii}$; (SEQ ID NO: 11)

C$_i$MEC$_{ii}$YMMEDGTC$_{iii}$; (SEQ ID NO: 12)

C$_i$LEC$_{ii}$NMMEDGTC$_{iii}$; and (SEQ ID NO: 13)

C$_i$(Nle)VC$_{ii}$H(Nle)(Nle)EDGTC$_{iii}$ (SEQ ID NO: 14)

or a pharmaceutically acceptable salt thereof.

4. The drug conjugate as defined in claim 1, wherein the pharmaceutically acceptable salt is selected from the group consisting of the free acid, the sodium salt, the potassium salt, the calcium salt, and the ammonium salt.

5. The drug conjugate as defined in claim 1, wherein the PSMA is human PSMA.

6. A pharmaceutical composition which comprises the drug conjugate as defined in claim 1, in combination with one or more pharmaceutically acceptable excipients.

7. The drug conjugate as defined in claim 1, wherein the molecular scaffold is 1,3,5-tris(bromomethyl)benzene (TBMB).

8. The drug conjugate as defined in claim 1, wherein the functional group is a cytotoxic agent.

9. The drug conjugate as defined in claim 8, wherein the cytotoxic agent is DM1 or MMAE.

10. The drug conjugate as defined in claim 1, wherein the one or more effector and/or functional groups is a metal chelator.

11. The drug conjugate as defined in claim 10, wherein the metal chelator is complexed to a metal radioisotope.

12. The drug conjugate as defined in claim 11, wherein the metal radioisotope is selected from $^{64}$Cu, $^{67}$Ga, $^{68}$Ga, $^{177}$Lu, $^{90}$Y, and $^{213}$Bi.

13. A drug conjugate comprising a peptide ligand, or a pharmaceutically acceptable salt thereof, conjugated to one or more effector and/or functional groups, wherein the peptide ligand is specific for prostate specific membrane antigen (PSMA) and is selected from the group consisting of:

ACMVCHMMEDGTCA; (SEQ ID NO: 18)

Ac-CMVCHMMEDGTC; (SEQ ID NO: 40)

ACMVCHMMEDGTCAGASPAAPSAPP; (SEQ ID NO: 17)

CIECYIMEDGTCA; (SEQ ID NO: 19)

CEECLTLEDGTCA; (SEQ ID NO: 20)

-continued

CEECFRLEDGTCA; (SEQ ID NO: 21)

EVCWDCFMMEDGTCA; (SEQ ID NO: 22)

(D-E)VCWDCFMMEDGTCA-Sar6-K; (SEQ ID NO: 23)

(B-Ala)-Sar5-EVCWDCFMMEDGTC; (SEQ ID NO: 24)

Ac-(D-E)VCWDCFMMEDGTCA-Sar6-K(Ac); (SEQ ID NO: 25)

Ac-(D-E)VCWDCF(Nle)(Nle)EDGTCA-Sar6-K; (SEQ ID NO: 26)

Ac-(D-E)VCWDCFMMEDGTCA-Sar6-(D-K); (SEQ ID NO: 27)

Ac-(D-E)VCWDCF(Nle)MEDGTCA-Sar6-(D-K); (SEQ ID NO: 28)

Ac-(D-E)VCWDCFM(Nle)EDGTCA-Sar6-(D-K); (SEQ ID NO: 29)

Ac-(D-E)VCWDCF(Nle)(Nle)EDGTCA-Sar6-(D-K); (SEQ ID NO: 30)

SVCRECYMMEDGTCA; (SEQ ID NO: 31)

FCSECYMMEDGTCA; (SEQ ID NO: 32)

LCMECYMMEDGTCA; (SEQ ID NO: 33)

(D-V)CLECNMMEDGTCA-Sar6-K; (SEQ ID NO: 34)

(B-Ala)-Sar5-VCLECNMMEDGTC; (SEQ ID NO: 35)

Ac-CMVCHMMEDGTCA-Sar6-K; (SEQ ID NO: 36)

(B-Ala)-Sar5-ACMVCHMMEDGTC; (SEQ ID NO: 37)

Ac-C(Nle)VCH(Nle)(Nle)EDGTCA-Sar6-K; (SEQ ID NO: 38)

(B-Ala)-Sar5-AC(Nle)VCH(Nle)(Ne)EDGTC. (SEQ ID NO: 39)

and wherein the cysteine residues form covalent bonds with a molecular scaffold to form at least two polypeptide loops.

14. The drug conjugate of claim 13, wherein the peptide ligand is selected from the group consisting of:

EVCWDCFMMEDGTCA; (SEQ ID NO: 22)

Ac-(D-E)VCWDCFM(Nle)EDGTCA-Sar6-(D-K); (SEQ ID NO: 29)

FCSECYMMEDGTCA; and (SEQ ID NO: 32)

LCMECYMMEDGTCA. (SEQ ID NO: 33)

* * * * *